US012763192B2

(12) United States Patent
Yamane et al.

(10) Patent No.: US 12,763,192 B2
(45) Date of Patent: Oct. 13, 2026

(54) IMAGE PROCESSING APPARATUS AND IMAGE PROCESSING METHOD

(71) Applicants: Canon Kabushiki Kaisha, Tokyo (JP); CANON MEDICAL SYSTEMS CORPORATION, Tochigi (JP)

(72) Inventors: Toshimizu Yamane, Ohta-ku (JP); Gakuya Soeda, Isehara (JP)

(73) Assignees: Canon Kabushiki Kaisha, Tokyo (JP); CANON MEDICAL SYSTEMS CORPORATION, Tochigi (JP)

( * ) Notice: Subject to any disclaimer, the term of this patent is extended or adjusted under 35 U.S.C. 154(b) by 210 days.

(21) Appl. No.: 18/821,223

(22) Filed: Aug. 30, 2024

(65) Prior Publication Data

US 2025/0078986 A1 Mar. 6, 2025

(30) Foreign Application Priority Data

Aug. 31, 2023 (JP) ................................ 2023-140632

(51) Int. Cl.
*G16H 30/00* (2018.01)
*G16H 30/20* (2018.01)

(52) U.S. Cl.
CPC .................................. *G16H 30/20* (2018.01)

(58) Field of Classification Search
CPC ......... G16H 30/20; G16H 30/40; G16H 50/20
See application file for complete search history.

(56) References Cited

U.S. PATENT DOCUMENTS

| | | | | |
|---|---|---|---|---|
| 10,755,810 | B2 * | 8/2020 | Buckler | G16H 30/40 |
| 11,417,000 | B2 | 8/2022 | Yamazaki et al. | |
| 2021/0065360 | A1 * | 3/2021 | Laaksonen | G06T 7/12 |
| 2021/0133977 | A1 * | 5/2021 | Yamazaki | G06V 10/82 |
| 2026/0031238 | A1 * | 1/2026 | Hanratty | G06V 10/26 |

FOREIGN PATENT DOCUMENTS

| | | | | |
|---|---|---|---|---|
| CN | 110335269 A | * 10/2019 | | G06V 10/82 |
| JP | 2021-69793 A | 5/2021 | | |

* cited by examiner

*Primary Examiner* — Ping Y Hsieh
(74) *Attorney, Agent, or Firm* — Oblon, McClelland, Maier & Neustadt, L.L.P.

(57) ABSTRACT

An image processing apparatus according to an embodiment includes processing circuitry configured to acquire medical image data; acquire, in relation to the medical image data, first region information representing a first region; acquire a first inference result by a first inference processing of applying a first inference model to first medical image data based on the medical image data, and a second inference result by a second inference processing of applying a second inference model to second medical image data based on the medical image data; and acquire, on the basis of the first region information, second region information that is a region satisfying a predetermined condition, from at least regions based on the first inference result or regions based on the second inference result. The processing circuitry is configured to acquire, as the second region information that is the region satisfying the predetermined condition: a region extending from the first region to outside of the first region, the region being among the regions based on the first inference result; or a region extending from the first region to the outside of the first region, the region being among the regions based on the second inference result.

15 Claims, 13 Drawing Sheets

IMAGE PROCESSING APPARATUS AND IMAGE PROCESSING METHOD

CROSS-REFERENCE TO RELATED APPLICATIONS

This application is based upon and claims the benefit of priority from Japanese Patent Application No. 2023-140632, filed on Aug. 31, 2023; the entire contents of which are incorporated herein by reference.

FIELD

Embodiments described herein relate generally to image processing apparatuses and image processing methods.

BACKGROUND

Diagnoses are made in the medical field by using images acquired by means of various medical image diagnosis apparatuses (also referred to as medical image capturing apparatuses or modalities). Furthermore, technologies for supporting diagnoses by detection of candidates for lesions, such as tumors, from images using machine learning techniques have been known. Specifically, inference processing using trained models (also referred to as inference models) enables acquisition of region information on lesion candidates from images and provision of the region information acquired as reference information for diagnoses to users, such as medical doctors.

Inference performance may vary by region in an image in inference processing using an inference model. For example, it has been known that when an image includes plural parts of a body, using a single inference model may not enable an inference to be made successfully because characteristics of tumors may differ from one part to another and that inference model may be not well-adapted to these different characteristics. Moreover, adopting a method of dividing an image into plural regions and making and integrating inferences using different inference models respectively for these regions (that is, combining plural models) may reduce precision of inference results for boundary portions of the regions.

DETAILED DESCRIPTION

Figure 1:
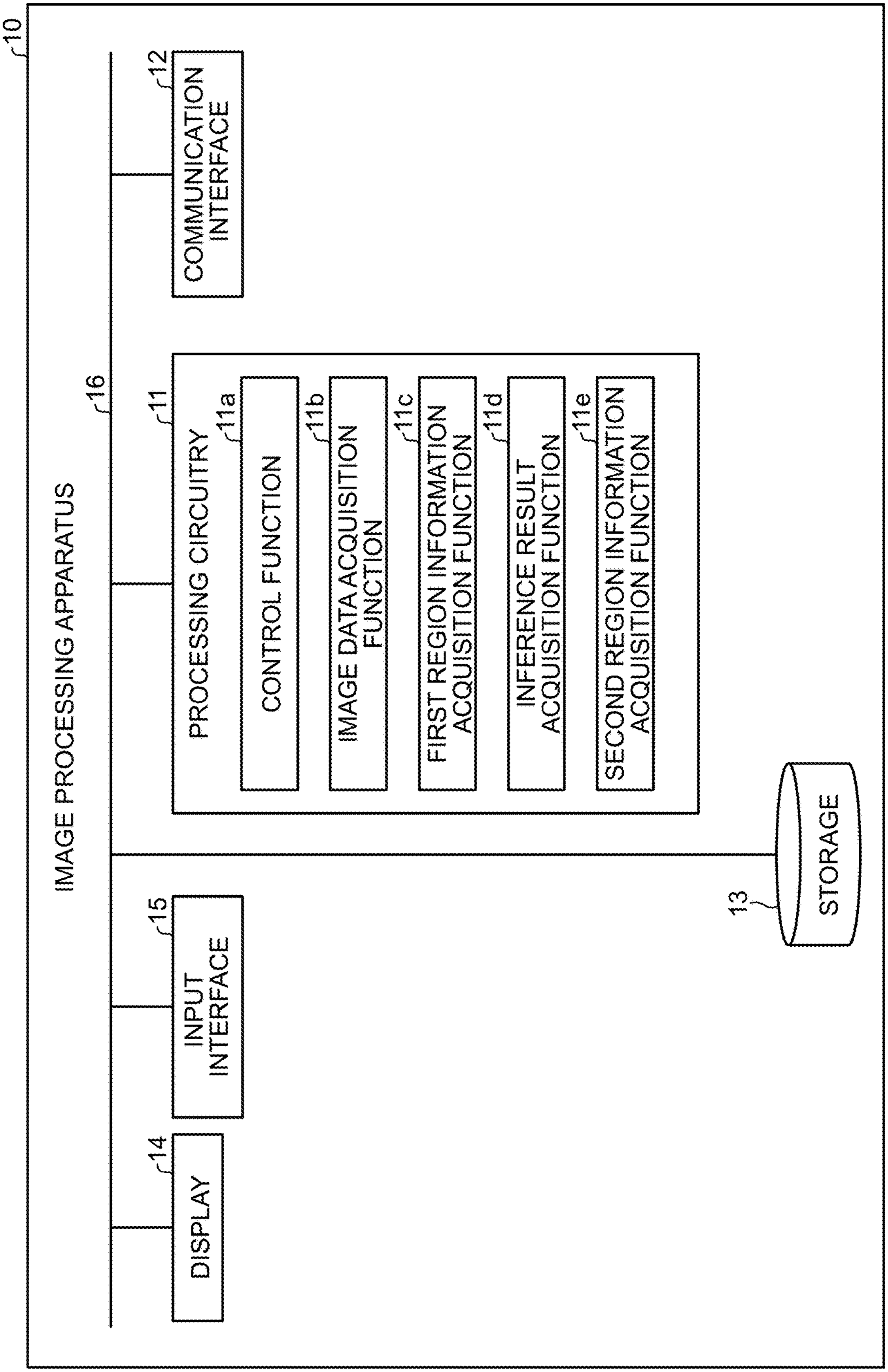
FIG. 1 is a diagram illustrating an example of an overall configuration of an image processing apparatus according to a first embodiment.

An image processing apparatus according to an embodiment includes processing circuitry. The processing circuitry is configured to acquire medical image data. The processing circuitry is configured to acquire, in relation to the medical image data, first region information representing a first region. The processing circuitry is configured to acquire a first inference result by a first inference processing of applying a first inference model to first medical image data based on the medical image data, and a second inference result by a second inference processing of applying a second inference model to second medical image data based on the medical image data. The processing circuitry is configured to acquire, on the basis of the first region information, second region information that is a region satisfying a predetermined condition, from at least regions based on the first inference result or regions based on the second inference result. The processing circuitry is configured to acquire the second region information that is the region satisfying the predetermined condition, the region being: a region extending from the first region to outside of the first region and being among the regions based on the first inference result; or a region extending from the first region to the outside of the first region and being among the regions based on the second inference result.

Preferred embodiments of an image processing apparatus and an image processing method will hereinafter be described in detail by reference to the appended drawings. Configurations described with respect to the following embodiments are just examples and the embodiments are not to be limited to the configurations illustrated in the drawings.

An image processing apparatus according to an embodiment is an apparatus that acquires region information (lesion candidate region information) on a lesion candidate, such as a tumor or a polyp, by inference processing based on machine learning, with medical image data serving as input, the medical image data being on a subject (for example, a patient). The image processing apparatus executes first inference processing using an inference model (a first inference model) dedicated to a specific part (a partial region), such as the head, the liver, or the large intestine, and second inference processing using an inference model (a second inference model) mainly for the whole body, and acquires region information on a lesion candidate by combining results of the first inference processing and the second inference processing. With respect to the embodiment, medical images will be described as an example a target to be processed, but the target to be processed is not to be limited to medical images.

FIG. 1 is a diagram illustrating an example of a configuration of an image processing apparatus 10 according to a first embodiment. As illustrated in FIG. 1, the image processing apparatus 10 has processing circuitry 11, a communication interface 12, a storage 13, a display 14, an input interface 15, and a connection unit 16. Furthermore, the image processing apparatus 10 is communicably connected to a medical image diagnosis apparatus (modality), a medical image storage apparatus, and/or department systems, for example, via a network not illustrated in the drawings.

Examples of the medical image diagnosis apparatus include a positron emission tomography (PET) apparatus, an X-ray computed tomography (CT) apparatus, a magnetic resonance imaging (MRI) apparatus, and an X-ray diagnostic apparatus. The medical image storage apparatus is implemented by a picture archiving and communication system (PACS), for example, and stores medical images captured by the medical image diagnosis apparatus in a format compatible with, for example, Digital Imaging and Communications in Medicine (DICOM). Examples of the department systems include various systems, such as a hospital information system (HIS), a radiology information system (RIS), a diagnostic report system, and a laboratory information system (LIS).

The processing circuitry 11 controls the image processing apparatus 10 by executing a control function 11*a*, an image data acquisition function 11*b*, a first region information acquisition function 11*c*, an inference result acquisition function 11*d*, and a second region information acquisition function 11*e*, according to input operation received from a user via the input interface 15. The image data acquisition function 11*b* is an example of an image data acquisition unit. The first region information acquisition function 11*c* is an example of an acquisition unit for first region information. The inference result acquisition function 11*d* is an example of an acquisition unit for an inference result. The second region information acquisition function 11*e* is an example of an acquisition unit for second region information.

The control function 11*a* generates various graphical user interfaces (GUIs) and various kinds of display information, according to operation via the input interface 15, and performs control for display on the display 14. The control function 11*a* also controls transmission and reception of information to and from an apparatus and/or a system on a network not illustrated in the drawings, via the communication interface 12. For example, the control function 11*a* acquires information related to a subject from an external system connected to the network. Furthermore, the control function 11*a* outputs a processing result to the apparatus and/or the system on the network.

On the basis of reference address information on an image (for example, any of a uniform resource locator (URL), various unique identifiers (UIDs), and a path character string), the image data acquisition function 11*b* acquires medical image data from the medical image diagnosis apparatus or the medical image storage apparatus, for example, the medical image data resulting from imaging of a subject by the medical image diagnosis apparatus. For example, the image data acquisition function 11*b* acquires a three-dimensional medical image (volume data) as the medical image data. Processing by the image data acquisition function 11*b* will be described in detail later.

The first region information acquisition function 11*c* acquires first region information that is region information representing a region of a specific part, such as the head, the liver, or the large intestine. Processing by the first region information acquisition function 11*c* will be described in detail later.

The inference result acquisition function 11*d* makes inferences with respect to the medical image data by using each of a first inference model and a second inference model and thereby acquires inference results. Processing by the inference result acquisition function 11*d* will be described in detail later.

The second region information acquisition function 11*e* acquires second region information (lesion candidate region information) that is region information on a lesion candidate, such as a tumor or a polyp, on the basis of the inference results acquired by the inference result acquisition function 11*d*. Processing by the second region information acquisition function 11*e* will be described in detail later.

The processing circuitry 11 is implemented by, for example, a processor. In this case, the above mentioned processing functions are stored in the storage 13 in the form of programs that are able to be executed by a computer. The processing circuitry 11 implements functions corresponding to the programs by reading and executing the programs stored in the storage 13. In other words, the processing circuitry 11 has the processing functions illustrated in FIG. 1 in a state of having read the programs.

The processing circuitry 11 may be composed of a combination of plural independent processors and the processing functions may be implemented by these processors executing the programs. Furthermore, any of the processing functions of the processing circuitry 11 may be implemented by being distributed to plural pieces of processing circuitry or integrated into a single piece of processing circuitry, as appropriate. The processing functions that the processing circuitry 11 has may be implemented by mixture of hardware, such as circuitry, and software. The case where the programs corresponding to the processing functions are stored in the single storage 13 has been described herein as an example, but the embodiments are not limited to this example. For example, in a configuration that may be adopted, the programs corresponding to the processing functions may be stored in plural storages in a distributed manner and the programs may be read and executed from the respective storages.

The communication interface 12 controls transmission and communication of various data transmitted and received between the image processing apparatus 10 and the other apparatus and/or system connected via the network. Specifically, the communication interface 12 is connected to the processing circuitry 11, and outputs data received from the other apparatus and/or system to the processing circuitry 11 or transmits data output from the processing circuitry 11 to the other apparatus and/or system. For example, the communication interface 12 is implemented by a network card, a network adapter, or a network interface controller (NIC).

The storage 13 stores therein various data and various programs. Specifically, the storage 13 is connected to the processing circuitry 11 and stores data input from the processing circuitry 11, or data stored in the storage 13 are read and output to the processing circuitry 11. For example, the storage 13 is implemented by: a semiconductor memory element, such as a random access memory (RAM) or a flash memory; a hard disk; and/or an optical disk.

The display 14 displays thereon various types of information and various data. Specifically, the display 14 is connected to the processing circuitry 11 and displays various types of information and various data output from the processing circuitry 11. For example, the display 14 is implemented by a liquid crystal display, a cathode ray tube (CRT) display, an organic EL display, a plasma display, or a touch panel.

The input interface 15 receives input operation for various instructions and various types of information, from a user. Specifically, the input interface 15 is connected to the processing circuitry 11, converts input operation received from the user into an electric signal, and outputs the electric signal to the processing circuitry 11. For example, the input interface 15 is implemented by a trackball, a switch button, a mouse, a keyboard, a touchpad where input operation is performed through a touch on an operation surface, a touch screen having a display screen and a touchpad that have been integrated with each other, a contactless input interface using an optical sensor, and/or a voice input interface. According to this specification, the input interface 15 is not necessarily an input interface having physical operation parts, such as a mouse and a keyboard. For example, examples of the input interface 15 also include electric signal processing circuitry that receives an electric signal corresponding to input operation from an external input device provided separately from the apparatus and outputs this electric signal to control circuitry.

The connection unit 16 is, for example, a bus that connects the processing circuitry 11, the communication interface 12, the storage 13, the display 14, and the input interface 15, to one another.

Figure 2:
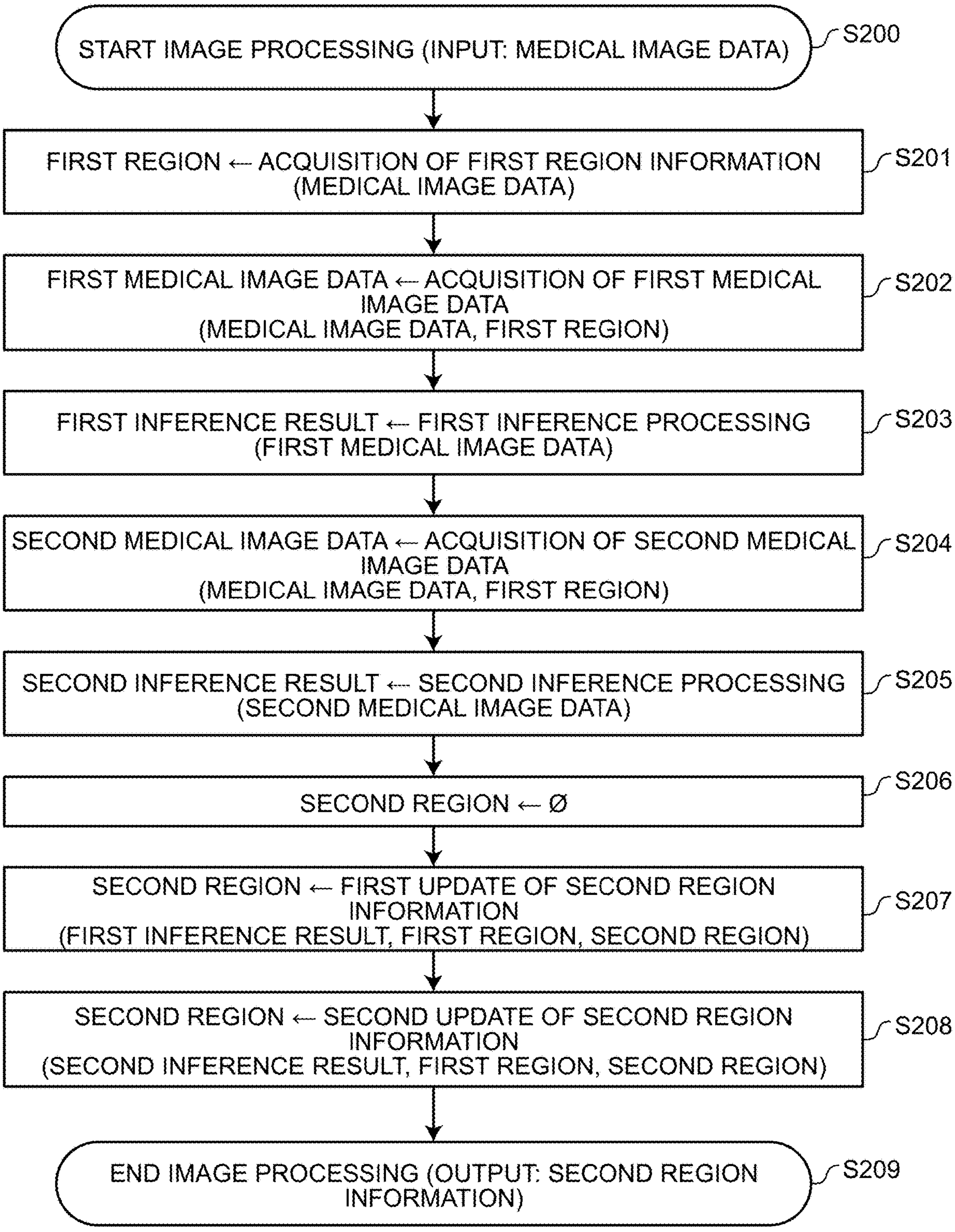
FIG. 2 is a flowchart illustrating an example of a process executed by the image processing apparatus according to the first embodiment.

FIG. 2 is a flowchart illustrating an example of a process executed by the image processing apparatus 10 according to the first embodiment. The image processing apparatus 10 makes various inferences, with medical image data resulting from imaging of a subject and serving as input, and outputs second region information describing a position of a lesion candidate (lesion candidate region information). The medical image data are three-dimensional volume data. An x-axis in an image coordinate system is set to increase in value toward the left hand from a subject, a y-axis therein to increase in value toward the back from the subject, and a z-axis to increase in value toward the head of the subject. It is assumed that a pixel value at coordinates, "(x, y, z)", of a medical image a can be referred to as "a [z, y, x]". Furthermore, it is assumed that a partial image having a rectangular range with diagonal points at coordinates "(x1, y1, z1)" and coordinates "(x2, y2, z2)" can be referred to as "a [z1: z2, y1: y2, x1: x2]". It is assumed that 0 has been specified if "x1, y1, z1" has been omitted. Furthermore, it is assumed that widths of an image along the respective axes have been specified if "x2, y2, z2" has been omitted.

An example of a process targeting medical image data acquired by PET-CT examination, in which PET examination and X-ray CT examination are simultaneously performed, will be described mainly with respect to this embodiment. However, the embodiment is not limited to this example, and is similarly applicable to image data from another modality, such as PET images, X-ray CT images, magnetic resonance imaging (MRI) images, and ultrasound images.

Processing of Step S201 illustrated in FIG. 2 is implemented by, for example, the processing circuitry 11 calling and executing a program corresponding to the first region information acquisition function 11*c* from the storage 13. Processing from Step S202 to Step S205 is implemented by, for example, the processing circuitry 11 calling and executing a program corresponding to the inference result acquisition function 11*d* from the storage 13. Processing from Step S206 to Step S208 is implemented by, for example, the processing circuitry 11 calling and executing a program corresponding to the second region information acquisition function 11*e* from the storage 13.

Step S200

In this embodiment, as illustrated by Step S200, the processing circuitry 11 starts image processing, with medical image data serving as input. For example, the processing circuitry 11 starts image processing determined by instruction operation via the input interface 15, with medical image data on a subject and serving as input. The medical image data are loaded into the processing circuitry 11 by the image data acquisition function 11*b* illustrated in FIG. 1.

Step S201

At Step S201, the first region information acquisition function 11*c* analyzes the medical image data acquired at Step S200 and acquires first region information representing a first region. For example, the first region information acquisition function 11*c* acquires, as the first region information, information representing a region of a specific part, such as the head, the liver, or the large intestine. Specific processing of Step S201 may be implemented by a different configuration, according to what kind of region the first region is. The processing of Step S201 according to this embodiment will hereinafter be described in detail by use of a flowchart in FIG. 3A to 3*c*.

When First Region is Region of Head

Figure 3A:
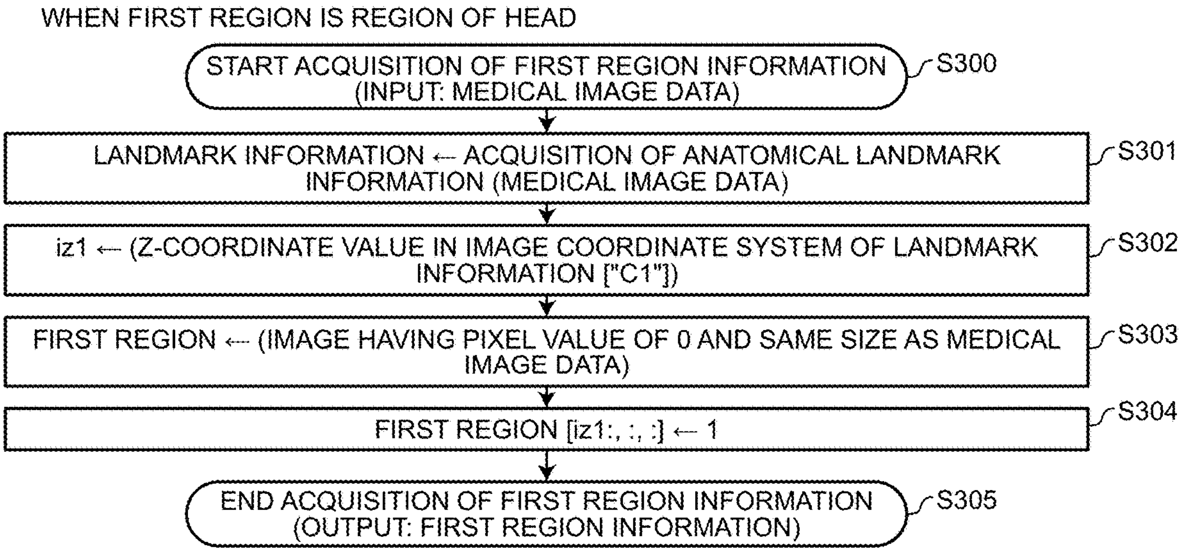
FIG. 3A is a flowchart illustrating an example of acquisition of first region information according to the first embodiment.

A processing sequence of Step S201 will be described by use of FIG. 3A for an example that is a case where the first region is a region of the head. In the case of FIG. 3A, the first region information acquisition function 11*c* starts acquisition of first region information, with medical image data serving as input, as illustrated by Step S300. Furthermore, the first region information acquisition function 11*c* outputs the first region information and ends the acquisition of the first region information, as illustrated by Step S305. Specifically, the first region information output at Step S305 is stored in, for example, the storage 13 and read and used as appropriate in later processing.

Step S301

At Step S301, the first region information acquisition function 11*c* acquires anatomical landmark information (for example, positions of landmarks) on a subject by using a known method, such as Random Forest, from the medical image data acquired at Step S200. In a case where the medical image data are image data by PET-CT examination, the anatomical landmark information is acquired by use of data on a CT image where structural features of body tissue are more visible.

Step S302

At Step S302, the first region information acquisition function 11*c* executes a process of determining a region representing the head in the medical image data. Specifically, a boundary position between the head and a region below the head is determined by use of a position of a landmark (for example, the atlas) positioned at a lower end of the head, the landmark being from the landmarks acquired at Step S301. More specifically, a z-coordinate (in the image coordinate system) of the atlas in the landmark information is set, by a z-coordinate of the lower end of the head being set to "iz1".

Step S303

At Step S303, the first region information acquisition function 11c prepares a mask image that is a three-dimensional image having the same size as the medical image data and having been initialized to zero. The mask image is an image with pixels having a pixel value of "1", the pixels being included in a target to be masked, and the other pixels having a pixel value of "0". The pixel values of this mask image are changed by processing at Step S304 described later.

Step S304

At Step S304, the first region information acquisition function 11c completes determination of a head region in the medical image data, that is, generation of the first region information, by changing all of pixel values of a region in the medical image data to "1", the region having z-coordinate values that are more toward the head than "iz1".

By the processing from Step S300 to Step S305 illustrated by FIG. 3A, the processing of Step S201 in the case where the first region is the head is executed. The first region acquired in this example specifically is a region corresponding to a region 601 in FIG. 5 and surrounding the head.

When First Region is Region of Large Intestine

Figure 3B:
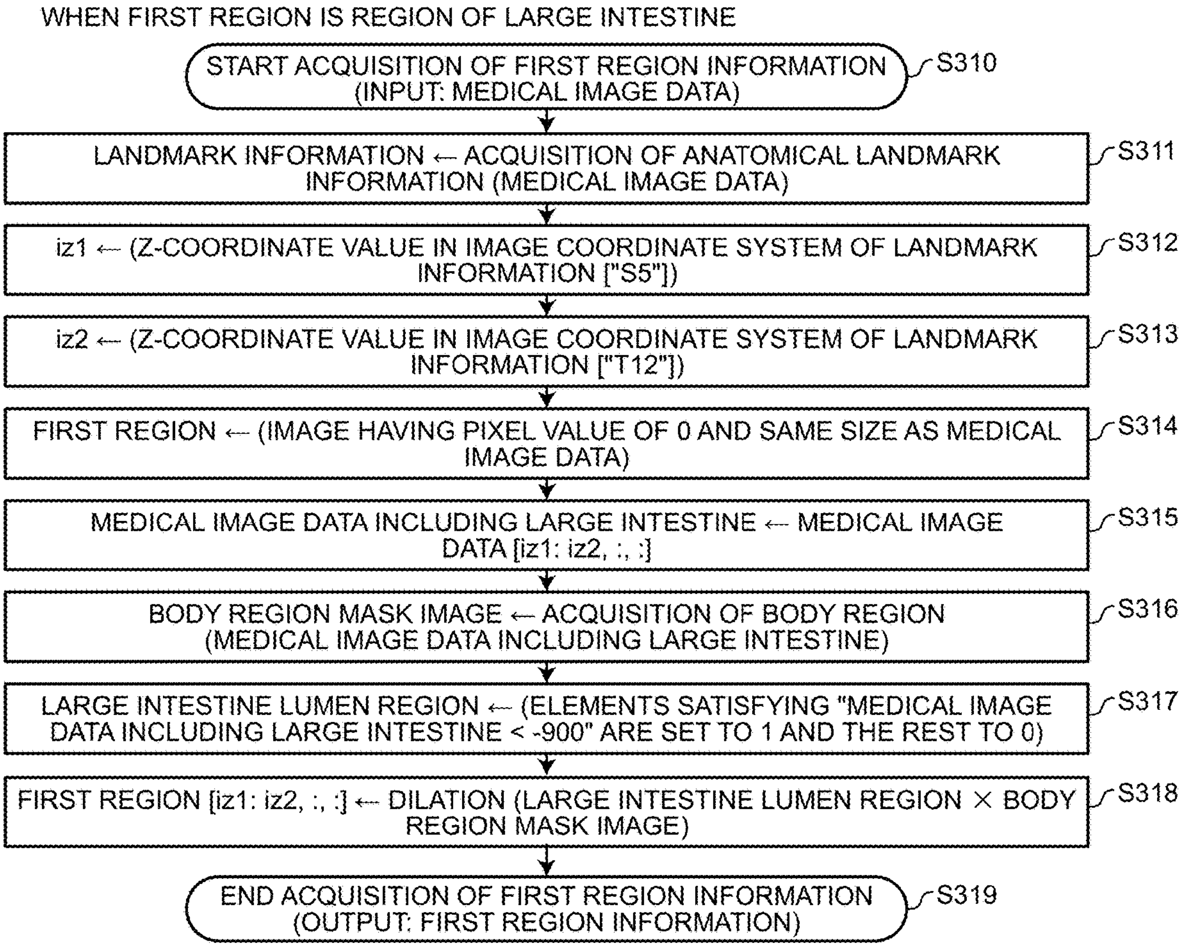
FIG. 3B is a flowchart illustrating an example of acquisition of first region information according to the first embodiment.

A processing sequence of Step S201 will be described by use of FIG. 3B for an example that is a case where the first region is a region of the large intestine. In the case of FIG. 3B, the first region information acquisition function 11c starts acquisition of first region information, with medical image data serving as input, as illustrated by Step S310. Furthermore, the first region information acquisition function 11c outputs the first region information and ends the acquisition of the first region information, as illustrated by Step S319. Specifically, the first region information output at Step S319 is stored in, for example, the storage 13 and read and used as appropriate in later processing.

Step S311

At Step S311, the first region information acquisition function 11c acquires anatomical landmark information on a subject by using a known method, such as Random Forest, from the medical image data acquired at Step S200. Specific processing is similar to the method described with respect to Step S301 and detailed description thereof will thus be omitted.

Step S312

At Step S312, the first region information acquisition function 11c executes a process of determining a position of a lower end of a region representing the large intestine in the medical image data. Anatomically, the position of the large intestine on the body axis is between the twelfth thoracic vertebra and the fifth sacral bone, and a z-coordinate (in the image coordinate system) of the fifth sacral bone in the landmark information is thus set at Step S312, by a z-coordinate of a lower end of the large intestine being set to "iz1".

Step S313

At Step S313, the first region information acquisition function 11c executes a process of determining a position of an upper end of a region representing the large intestine in the medical image data. Specifically, a z-coordinate (in the image coordinate system) of the twelfth thoracic vertebra in the landmark information is set, by a z-coordinate of the upper end of the large intestine being set to "iz2".

Step S314

At Step S314, the first region information acquisition function 11c prepares a mask image that is a three-dimensional image having the same size as the medical image data and having been initialized to zero. This processing step is similar to that of Step S303 described above and detailed description thereof will thus be omitted.

Step S315

At Step S315, the first region information acquisition function 11c cuts out an image having a range, "iz1: iz2", from the medical image data and generates medical image data including the large intestine.

Step S316

At Step S316, the first region information acquisition function 11c acquires a body region mask image by analyzing the medical image data including the large intestine by using a known algorithm, such as threshold processing, morphological operations, or labeling. A region in the body region mask image and having a pixel value of 1 represents a body region and a region therein and having a pixel value of "0" represents the outside of the body region (the atmosphere and a couch).

Step S317

At Step S317, the first region information acquisition function 11c acquires a large intestine lumen region that is a region (including an air region outside the body region) having CT values lower than about "−900", from the medical image data including the large intestine. This processing enable acquisition of the large intestine lumen region because the large intestine is generally inflated with air or carbon dioxide in CT colonography.

Step S318

At Step S318, the first region information acquisition function 11c excludes an air region outside the body region by multiplying (multiplication per element) each pixel value in the large intestine lumen region by a corresponding pixel value in the body region mask image. A region including the large intestine wall is acquired by dilation of a result of this multiplication, the dilation using morphology operations, this region is substituted into a predetermined slice of the first region, and generation of the first region information is thereby completed.

Through the processing from Step S310 to Step S319 illustrated by FIG. 3B, the processing of Step S201 in the case where the first region is the region of the large intestine is executed.

When First Region is Liver

Figure 3C:
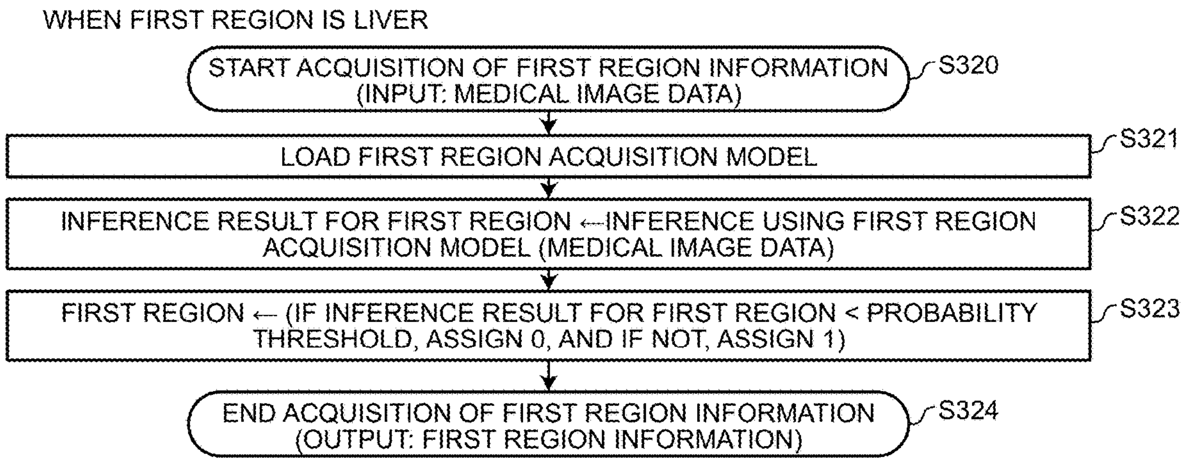
FIG. 3C is a flowchart illustrating an example of acquisition of first region information according to the first embodiment.

The processing sequence of Step S201 will be described by use of FIG. 3C for an example that is a case where the first region is the liver. In the case of FIG. 3C, the first region information acquisition function 11c starts acquisition of first region information, with medical image data serving as input, as illustrated by Step S320. Furthermore, the first region information acquisition function 11c outputs the first region information and ends the acquisition of the first region information, as illustrated by Step S324. Specifically, the first region information output at Step S324 is stored in, for example, the storage 13 and read and used as appropriate in later processing.

Step S321

At Step S321, the first region information acquisition function 11c loads a first region information acquisition model that is a model for acquisition of a region of the liver, from the storage 13 into the processing circuitry 11.

Step S322

At Step S322, the first region information acquisition function 11c acquires an inference result for the first region by making an inference using the model, with respect to the medical image data. The first region information acquisition model is a set of parameters to be used in inference processing, and the inference processing itself is able to be implemented by a known inference technique, such as U-Net. In this embodiment, an inference result is represented by a three-dimensional image and each pixel value in the image represents a probability that the pixel is included in the first region, but the method of representing an inference result, according to the present invention, is not limited to this embodiment and an inference result may be represented as a mask image that is the same as the first region.

Step S323

At Step S323, the first region information acquisition function 11*c* assigns "0" or "1" to each pixel of the inference result, with a probability threshold being a boundary value, and acquires the first region. The probability threshold used herein has a value of about "0.5".

Through the processing from Step S320 to Step S324 illustrated by FIG. 3C, the processing of Step S201 in the case where the first region is the liver is executed.

In these examples illustrated in FIG. 3A to 3C, in which the first region information is acquired, the first region is represented as a mask image with pixel values of an image corresponding to a portion included in the region being set to "1" and the rest being set to "0". However, the embodiment is not limited to this method of representation, and in one method of representing the first region information, the first region information may be represented by coordinate values of a bounding box of the region or a set of the coordinate values. The method of acquiring the first region information is not limited to the methods described above, and any organ recognition method or organ segmentation method based on image processing or machine learning may be used. In a configuration that may be adopted instead, the first region information is acquired from the outside, or the first region information is input by a user via a UI not illustrated in the drawings. Furthermore, the specific part may be an organ other than the head, the large intestine, and the liver, and may be a combination of plural parts (for example, the whole abdomen or the whole thorax and abdomen).

Step S202

At Step S202, the inference result acquisition function 11*d* acquires first medical image data corresponding to a region to be subjected to first inference processing, from the medical image data. Specifically, the inference result acquisition function 11*d* executes a process of cutting out a range wider than the first region acquired at Step S201 from the medical image data. The range has been made wider such that a tumor or a polyp having a possibility of straddling or extending over a boundary of the first region fits in the range and the range is able to be determined from, for example, training data for the first inference model. Specifically, in a method that may be adopted, a typical size of the tumor or polyp is determined from the training data, for example, and the region is extended by an amount corresponding to a size that is about the same as that typical size. Dilation by morphology operations may be used, for example, as the method of increasing the range of the region. The example where the region is extended by morphology operations has been described, but the embodiment is not limited to this example, and the region may be extended by other image processing. For example, in a case where the first region is a region of the large intestine, image data in a bounding box surrounding the first region may serve as the first medical image data. The first medical image data acquired in this embodiment are specifically an image corresponding to an image of a region 602 illustrated in FIG. 5, the image being of a region that goes out of the first region 601 a little.

The first medical image data may be acquired by another method as long as the first medical image data include a range resulting from addition of a margin to the first region. For example, a slice image group resulting from addition of a predetermined number of adjacent slice images serving as margins to all of slice images including the first region may serve as the first medical image data. Furthermore, the whole medical image data may serve as the first medical image data. In this case, a process of excluding any unnecessary region, such as a region outside the body, from the first medical image data may be performed, for example.

Step S203

At Step S203, the inference result acquisition function 11*d* performs the first inference processing, with respect to the first medical image data. Specifically, the inference result acquisition function 11*d* loads the first inference model into the processing circuitry 11 first, makes an inference using the first inference model for the first medical image data, and acquires a first inference result.

An inference model herein is a set of parameters used in inference processing. For example, the first inference model is a model that has been trained to be adapted to characteristics of an image in the first region representing the specific part. In this embodiment, for example, the first inference model is a model that has been built for extraction of a lesion candidate region (for example, a tumor region) from a PET-CT image of the head, large intestine, or liver, through inference. The inference processing itself is able to be implemented by a known inference technique, such as U-Net, and involves inference for calculation of a discrimination (a probability) on whether each position in the image is in the lesion candidate region. A range, for which an inference is made by use of the first inference model is the entire region of the first medical image data including the outside of the first region. In this embodiment, an inference result is represented by a three-dimensional image, and each pixel value of the image represents a probability that the pixel is included in a lesion candidate region. However, a method of representing an inference result is not limited to that of the embodiment, and a lesion candidate region may be represented as a mask image, for example.

Step S204

At Step S204, the inference result acquisition function 11*d* executes a process of cutting out second medical image data including a region to be subjected to second inference processing, from the medical image data acquired at Step S200. A specific process of Step S204 may be executed by a different configuration, according to what type of region the region to be subjected to the second inference processing is.

In a case where the region to be subjected to the second inference processing is "the whole body including the first region", the medical image data acquired at Step S200 directly serve as the second medical image data. That is, an image including the first medical image data including the first region serves as the second medical image data.

In a case where the region to be mainly subjected to the second inference processing is "the whole body other than the first region", a cut-out range for the second medical image data is set such that the range of the second medical image data overlaps the first region. Specifically, a first contracted region resulting from contraction of the first region is acquired. Subsequently, an area other than a region corresponding to the first contracted region is cut out from the medical image data and the second medical image data are thereby acquired. The range is caused to overlap the first region such that a tumor having a possibility of straddling or extending over the boundary of the first region fits in the overlapping range and the extent of this overlap is able to be determined from, for example, a presumed size of the tumor.

Figure 5:
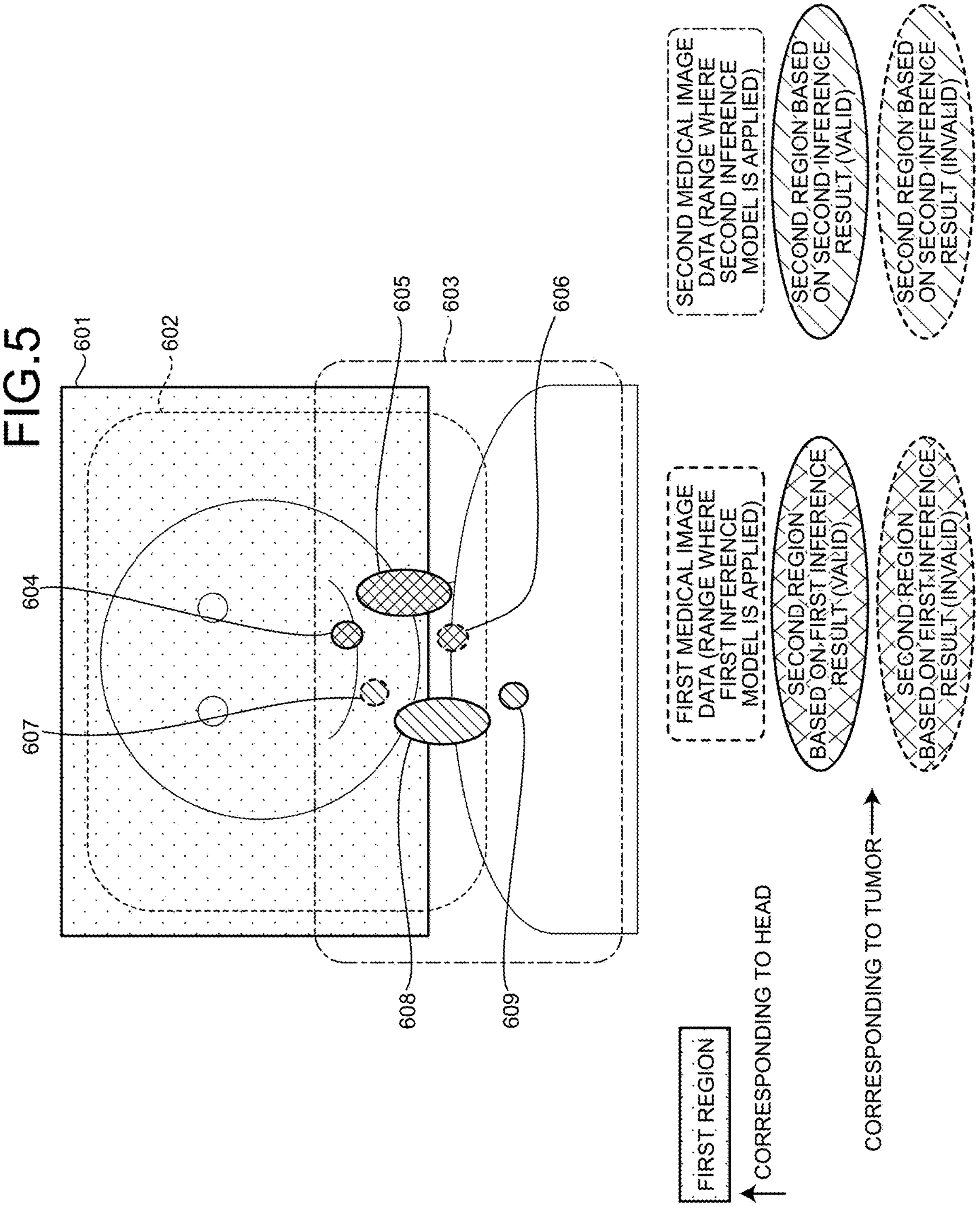
FIG. 5 is an example of a first region and a second region, according to the first embodiment.

The second medical image data acquired in this embodiment correspond specifically to an image of a region 603 illustrated in FIG. 5, the image being of a region having part thereof overlapping the first region 601.

The second medical image data may be acquired by another method as long as the second medical image data include a range resulting from addition of a margin to a region other than the first region. For example, a slice image group resulting from addition of a predetermined number of adjacent slice images serving as margins to all of slice images not including the first region may serve as the second medical image data. Furthermore, the whole medical image data may serve as the second medical image data. The second medical image data do not need to include all of the region other than the first region, and a process of excluding any unnecessary region, such as a region outside the body, may be performed.

Step S205

At Step S205, the inference result acquisition function 11*d* performs the second inference processing with respect to the second medical image data by using the second inference model. The specific method of the processing is similar to Step S203, but in this processing step, the image to be processed and the inference model are different. The second inference model used in this processing step is a model that is different from the first inference model used at Step S203 and that has been trained to be adapted also to characteristics of an image outside the first region. Specifically, the first inference model is a model that has been built for extraction of a lesion candidate from the medical image data on the specific part (the head, large intestine, or liver), but the second inference model is a model that has been built for extraction of a lesion candidate from a medical image of the region other than the specific part. Inference processing having characteristics different from those of the first inference processing is thereby performed in the second inference processing.

Step S206

At Step S206, the second region information acquisition function 11*e* prepares the second region information in an empty state, as illustrated by "φ" in FIG. 2. In this embodiment, the second region information is a mask image that sets pixel values of an image corresponding to a portion included in a region represented by the second region information to "1" and the rest to "0". However, the method of representing the second region information is not limited to this representation method, and the second region information may be represented by coordinate values of a bounding box of the region or a set of the coordinate values.

The second region prepared by the above described processing is updated by processing of Step S207 and Step S208 described later. The first inference result and the second inference result are thereby integrated with each other.

Step S207

Figure 4A:
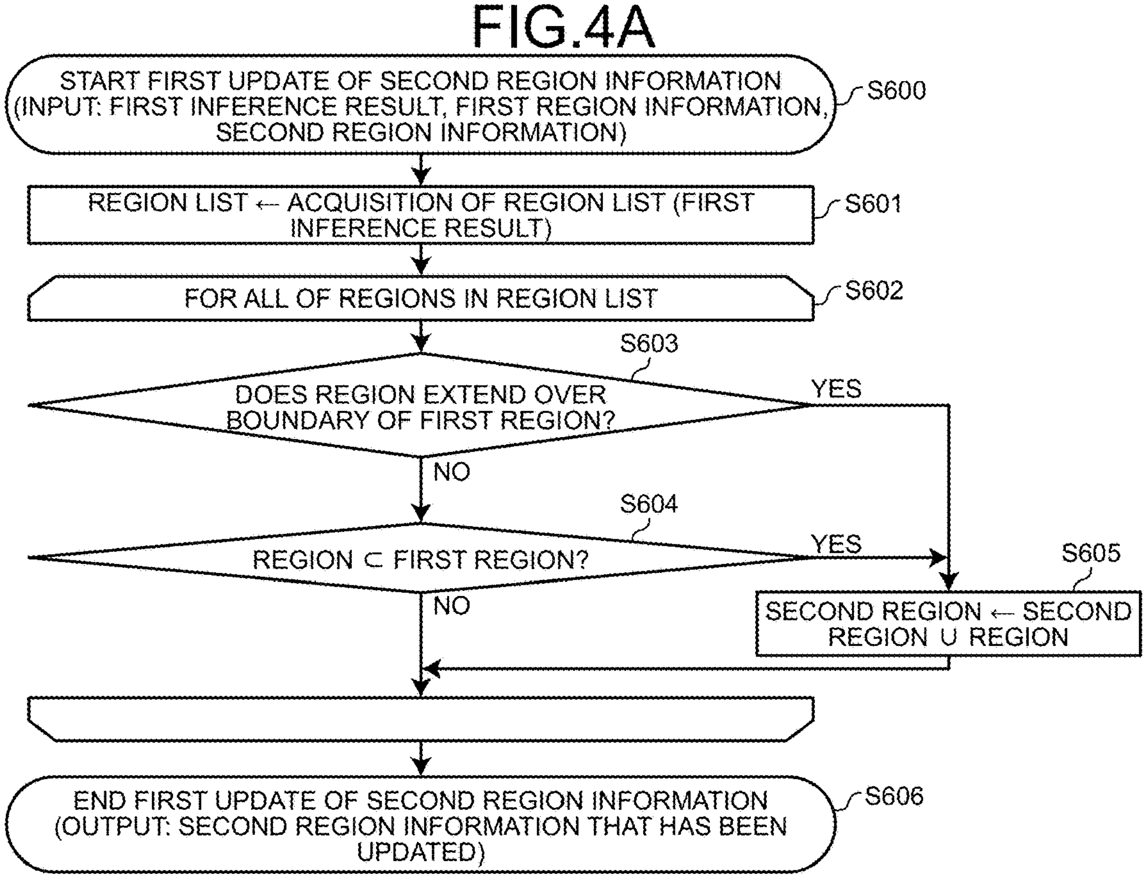
FIG. 4A is a flowchart illustrating an example of update of second region information according to the first embodiment.

At Step S207, the second region information acquisition function 11*e* updates the second region information by using the first inference result. A specific processing sequence of this processing step will be described in detail by use of FIG. 4A. In the case of FIG. 4A, the second region information acquisition function 11*e* starts a first update of the second region information, with the first inference result, the first region information, and the second region information all serving as input, as illustrated by Step S600. Furthermore, the first region information acquisition function 11*c* outputs the updated second region information and ends the first update of the second region information, as illustrated by Step S606. Specifically, the second region information output at Step S606 is stored in, for example, the storage 13 and read and used as appropriate in later processing.

Step S601

At Step S601, the second region information acquisition function 11*e* acquires a list of regions that are candidates for the second region, from the first inference result. More specifically, firstly, each pixel of the first inference result acquired at Step S203 is binarized with a predetermined threshold (for example, "0.5"). Subsequently, the binarized result is labelled by a known method and a region assigned to each label is recorded. That is, each block that is a continuous region resulting from the binarization of the first inference result is recorded in the list of regions.

Step S602

Steps S603 to S605 are repeated for each of target regions that are all of the regions in the list of regions acquired at Step S601.

Step S603

At Step S603, the second region information acquisition function 11*e* determines whether or not a target region straddles or extends over the boundary of the first region. This determination is able to be made by use of the following conditional expression (1), for example.

$$(\text{TARGET REGION} \cap \text{FIRST REGION} \neq \emptyset) \text{ AND } (\text{TARGET REGION} \cap \neg(\text{FIRST REGION}) \neq \emptyset) \quad (1)$$

In a case where the conditional expression (1) is true, the target region is determined to be straddling or extending over the boundary of the first region and the processing thus advances to the Yes branch to proceed to Step S605. If that is not the case, the processing advances to the No branch to proceed to Step S604. The case where "Yes" is the result of the determination at this processing step corresponds to a case where the target region corresponds to a region 605 illustrated in FIG. 5 and is a region that has gone out of the first region 601.

Step S604

At Step S604, the second region information acquisition function 11*e* determines whether or not the target region is completely included in the first region. In a case where a result of this determination is "Yes", the processing is advanced to Step S605. In a case where a result of the determination is "No", processing of an internal loop of a loop process through Step S602 is ended. The case where "Yes" is the result of the determination at this processing step corresponds to a case where the target region corresponds to a region 604 illustrated in FIG. 5 and is a region that is completely included in the first region 601. The case where "No" is the result of the determination at this processing step corresponds to a case where the target region corresponds to a region 606 illustrated in FIG. 5 and is a region that is outside the first region 601.

Step S605

At Step S605, the second region information acquisition function 11*e* executes a process of adding the target region to the second region. For example, in the example illustrated in FIG. 5, the region (605) straddling or extending over the boundary of the first region and the region (604) completely included in the first region are added to the second region.

Through the processing from Step S600 to Step S606 illustrated in FIG. 4A, the processing of Step S207 is executed. Any region having at least part thereof included in the first region is acquired as the second region, from the regions of the first inference result acquired by Step S203.

That is, a region excluding any region having no part thereof included in the first region is acquired as the second region from the first inference result.

In a case where the first inference result is sufficiently reliable (with little erroneous detection) even for the outside of the first region, all of regions in the list of regions may be acquired as the second region without excluding any region having no part thereof included in the first region. In this case, at Step S602, the second region information acquisition function 11*e* executes a process of adding all of the regions in the list of regions to the second region without executing the processing from Step S603 to Step S605.

Step S208

Figure 4B:
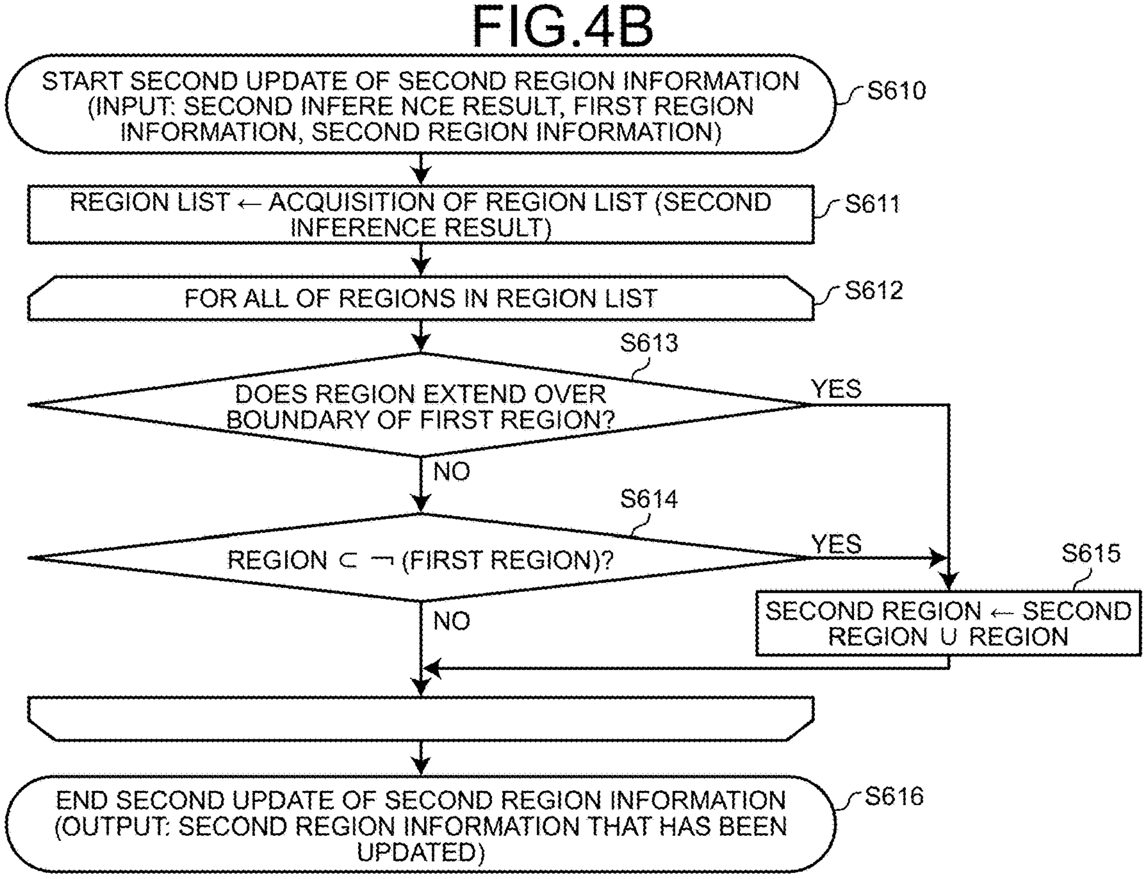
FIG. 4B is a flowchart illustrating an example of update of second region information according to the first embodiment.

At Step S208, the second region information acquisition function 11*e* updates the second region information by using the second inference result. A specific processing sequence of this processing step will be described in detail by use of FIG. 4B. In the case of FIG. 4B, the second region information acquisition function 11*e* starts a second update of the second region information, with the second inference result, the first region information, and the second region information all serving as input, as illustrated by Step S610. Furthermore, the second region information acquisition function 11*e* outputs the updated second region information and ends the second update of the second region information, as illustrated by Step S616. Specifically, the second region information output at Step S616 is stored in, for example, the storage 13 and read and used as appropriate in later processing.

Step S611

At Step S611, the second region information acquisition function 11*e* acquires a list of regions that are candidates for the second region, from the second inference result. More specifically, firstly, each pixel of the second inference result acquired at Step S205 is binarized with a predetermined threshold (for example, "0.5"). Subsequently, the binarized result is labelled by a known method and a region assigned to each label is recorded into a list of regions.

Step S612

Steps S613 to S615 are repeated for each of target regions that are all of the regions in the list of regions acquired at Step S611.

Step S613

At Step S613, the second region information acquisition function 11*e* determines whether or not a target region straddles or extends over the boundary of the first region. This determination is able to be made by use of the conditional expression (1), for example, similarly to Step S603.

In a case where the conditional expression (1) is true, the processing advances to the Yes branch to proceed to Step S615. If that is not the case, the processing advances to the No branch to proceed to Step S614. The case where "Yes" is the result of the determination at this processing step corresponds to a case where the target region corresponds to a region 608 illustrated in FIG. 5 and is a region that has entered the first region 601.

Step S614

At Step S614, the second region information acquisition function 11*e* determines whether or not the target region is completely included in the "region other than the first region". In a case where a result of this determination is "Yes", the processing is advanced to Step S615. In a case where a result of the determination is "No", processing of an internal loop of a loop process through Step S612 is ended. The case where "Yes" is the result of the determination at this processing step corresponds to a case where the target region corresponds to a region 609 illustrated in FIG. 5 and is a region outside the first region 601. The case where "No" is the result of the determination at this processing step corresponds to a case where the target region corresponds to a region 607 illustrated in FIG. 5 and is a region that is completely included in the first region 601.

Step S615

At Step S615, the second region information acquisition function 11*e* executes a process of adding the target region to the second region. For example, in the example illustrated in FIG. 5, the region (608) straddling or extending over the boundary of the first region and the region (609) completely included in the "region other than the first region" are added to the second region.

Through the processing from Step S610 to Step S616 illustrated in FIG. 4B, the processing of Step S208 is executed. The second region information based on the second inference result including any region that has entered the first region is thereby obtained. That is, a region excluding any region having no part thereof included in the first region is acquired as the second region from the second inference result.

In a case where the second inference result is sufficiently reliable (with little erroneous detection) even for the inside of the first region, all of regions in the list of regions may be acquired as the second region without excluding any region having no part thereof outside the first region. For example, in the example illustrated in FIG. 5, the region (607) having no part thereof included in the "region outside the first region" may be added to the second region. In this case, at Step S612, the second region information acquisition function 11*e* executes a process of adding all of the regions in the list of regions to the second region without executing the processing from Step S613 to Step S615.

Furthermore, the second region information is acquired as follows, through the processing of Step S207 and the processing of Step S208. That is, regions acquired are: any region having at least part thereof included in the first region, the region being among lesion candidate regions acquired by the first inference processing; and any region having at least part thereof being outside the first region, the region being among lesion candidate regions acquired by the second inference processing. Regions that may be excluded from the lesion candidate regions then are: any region having no part thereof included in the first region, the region being among the lesion candidate regions acquired by the first inference processing; and any region having no part thereof being outside the first region, the region being among the lesion candidate regions acquired by the second inference processing. An effect that is thereby able to be expected is an effect of reducing false positives resulting from extension of the processing range to a part not presumed by each inference model.

Furthermore, a region extending from the first region to the outside of the first region may be included in the lesion candidate regions, the region being among the lesion candidate regions acquired by the first inference processing and/or the second inference processing. An effect that is able to be thereby expected is an effect of reducing false negatives resulting from division of tumor candidates at joint portion.

Furthermore, in the processing of Step S605 or S615 in FIG. 4A to 4B, whether or not a "straddling region", for which a result of the determination at Step S603 or S613 is Yes, is to be added to the second region may be determined on the basis of whether or not the "straddling region" has a size (specifically, a volume or an area) equal to or larger than a predetermined size. Furthermore, because each pixel value of an image of an inference result represents a probability that the pixel is included in a lesion candidate region of the inference result, whether or not a "straddling region" is to be added to the second region may be determined on the basis of whether a probability of the region is equal to or larger than a predetermined value. That is, this determination may be made on the basis of whether or not the sum total of probabilities that pixels in that region are included in the second region (or the largest value, the median, the mean value, or the smallest value of the probabilities) is equal to or larger than a predetermined value. A threshold of the size or probability needs to be determined so that false positives are generated as few as possible, and may be determined, for example, from the training data for the inference models. Furthermore, the second region information acquisition function 11*e* may determine whether or not a "straddling region" is to be added to the second region, according to whether or not the region is a continuous region.

Figure 6:
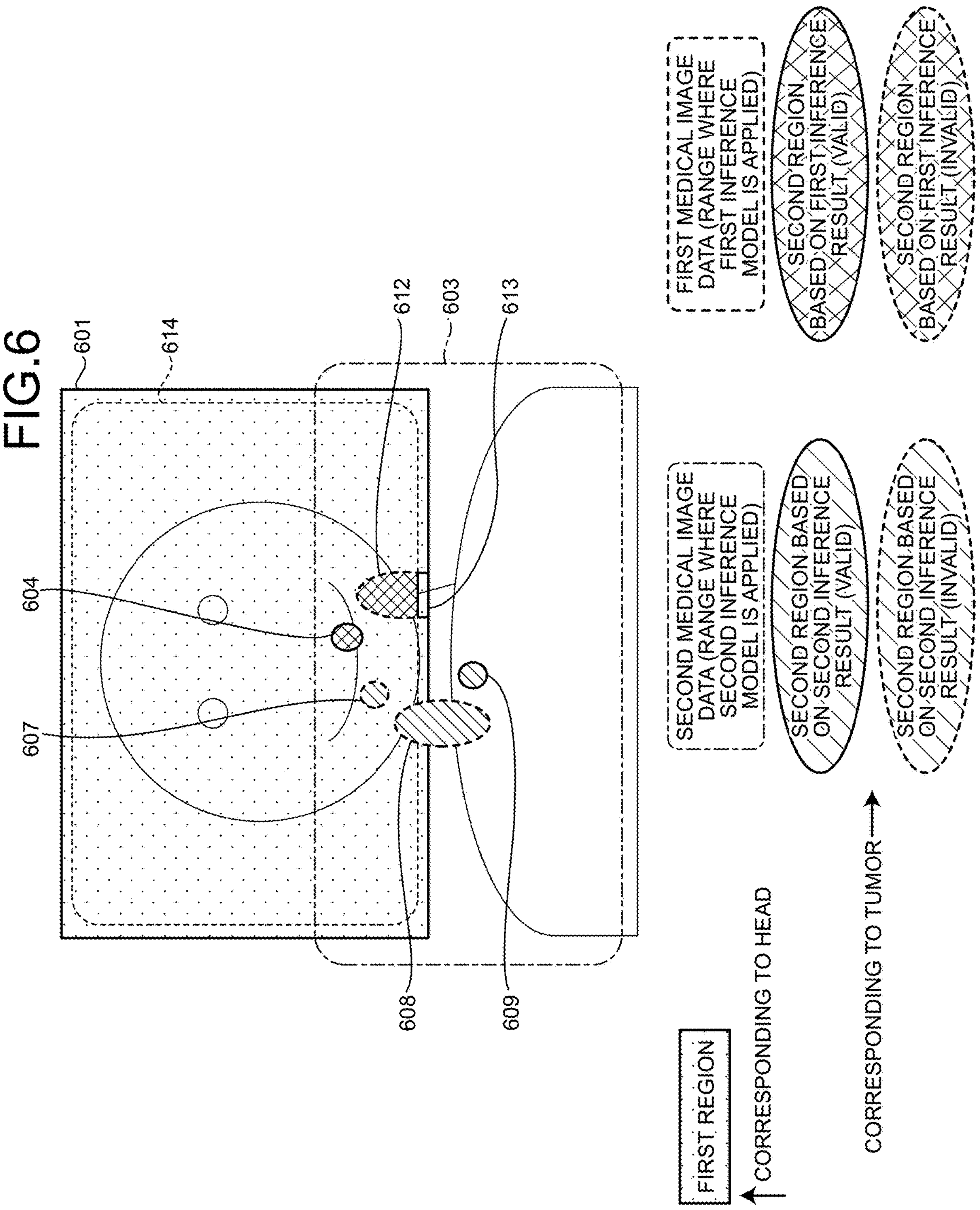
FIG. 6 is a special example of the first region and the second region, according to the first embodiment.

In addition, in the processing of Step S603 or S613 in FIG. 4A to 4B, whether the region is straddling the boundary of the first region may be determined on the basis of a region in contact with the boundary of the first region. That is, for example, a determination may be made on the basis of whether an area intersecting an end face of the first region is large. This determination method is effective also for a case where the first region (601) and the first medical image data (614) have the same range, as illustrated in FIG. 6. That is, in a case where an area (613) intersecting the end face of the first region is large, even if there is actually no region going out of the first region, that region (612) is able to be regarded as a region extending from the first region to the outside of the first region.

Furthermore, the processing circuitry 11 outputs the second region information and ends the image processing, as illustrated by Step S209. For example, at Step S209, the control function 11*a* stores (saves) the second region information acquired by the processing from Step S200 to Step S208 into the storage 13 or causes the display 14 to display the second region information. For example, a user, such as medical doctor, is able to refer to the second region information displayed on the display 14, as reference information for diagnosis.

As described above, using the image processing apparatus according to this embodiment enables improvement of inference performance in a case where plural models are combined in inference processing based on machine learning for acquisition of region information on lesion candidates.

It has been known that an inference cannot be successfully made when inference processing is performed with a single inference model, because of differences between characteristics of different regions. For example, with PET apparatuses, tumor portions are captured brightly but not only tumor portions but also non-tumor portions are brightly captured in brain regions. Therefore, it has been known that using a single inference model for the whole body in detecting tumors by machine learning from a PET image does not enable an inference to be made successfully because the single inference model is not adapted to the different characteristics.

Accordingly, a method of making an inference using a trained model different from that for other regions for a region adjacent to a different part has been disclosed in Patent Literature 1, for example. However, integrating inferences respectively made using different models for plural regions reduces precision of inference results for boundaries of the regions.

With respect to this issue, the image processing apparatus according to the first embodiment enables reduction of erroneous detection for boundaries of regions as described above and improvement of inference performance, while using plural inference models in inference processing based on machine learning for acquisition of region information on lesion candidates.

The flowchart illustrated in FIG. 2 is just an example, and the specific processing sequence may be modified as appropriate. For example, the processing of preparing the second region information in an empty state at Step S206 may be executed before Step S205. Furthermore, the output processing is illustrated as Step S209 in FIG. 2, but at each of Steps S201 to S208, a result of that step may be output as appropriate. For example, the control function 11*a* may store a result of Step S201 into the storage 13 or cause the display 14 to display the result, the result being the first region information acquired at Step S201. Similarly, the specific processing sequences of flowcharts other than that of FIG. 2 may be modified as appropriate.

The process of acquiring first region information by inference using an inference model based on machine learning has been described as an example of the processing at Step S201 according to the first embodiment. The model used in this inference may be additionally trained using a result of acquisition of the second region information. An example of this case will be described as a second embodiment. Medical images will be described as an example of a target to be processed with respect to the second embodiment, but the target to be processed is not limited to medical images.

Figure 7:
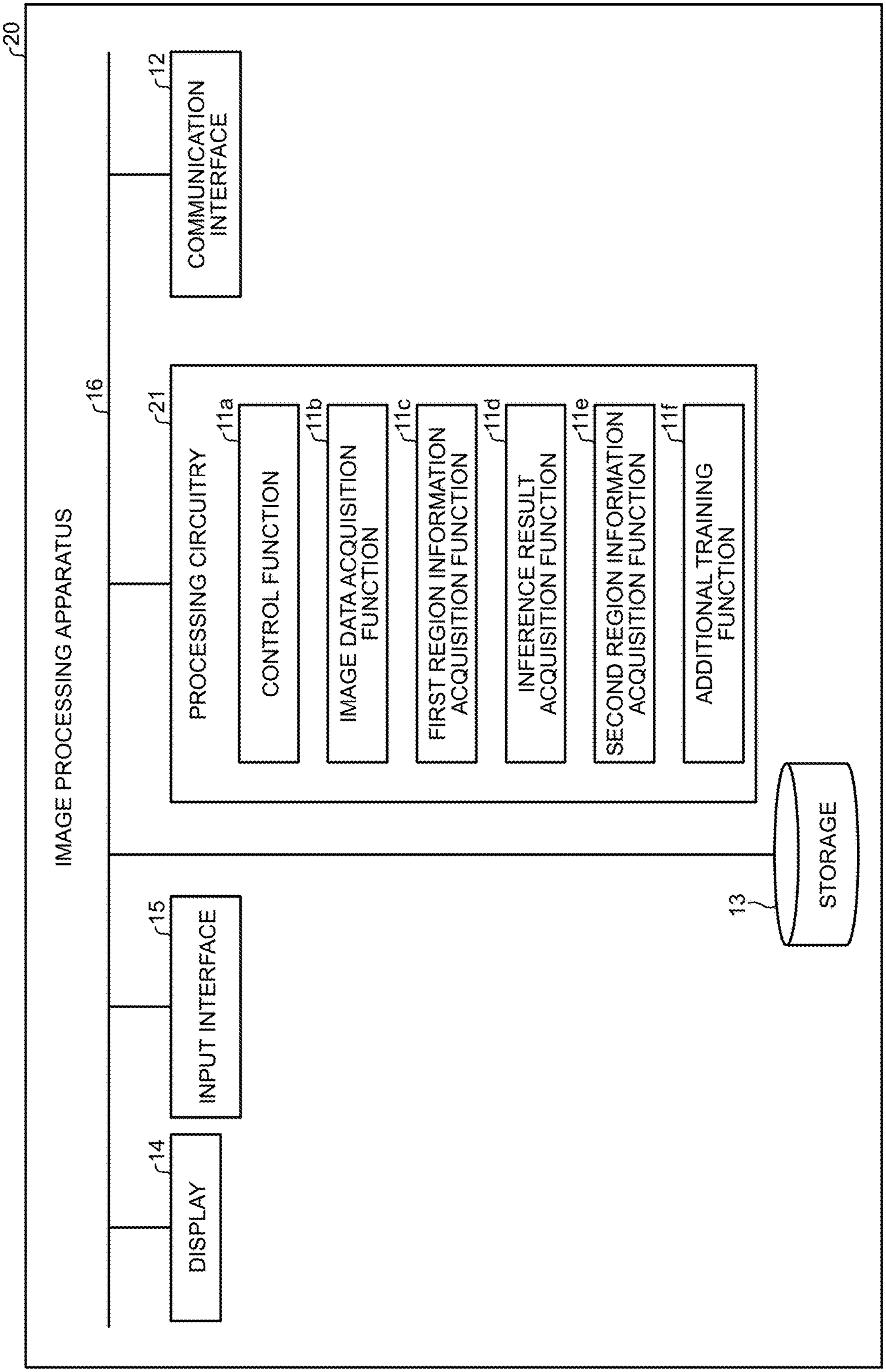
FIG. 7 is a diagram illustrating an example of an overall configuration of an image processing apparatus according to a second embodiment.

FIG. 7 illustrates an overall configuration of an image processing apparatus 20 according to the second embodiment. Processing by a second region information acquisition function 11*e* of processing circuitry 21 according to the second embodiment is different from that of the processing circuitry 11 according to the first embodiment. Furthermore, the processing circuitry 21 according to the second embodiment additionally has an additional training function 11*f*, as compared to the processing circuitry 11 according to the first embodiment. The additional training function 11*f* is an example of an additional training unit. The following description will mainly be on these functions.

Figure 8:
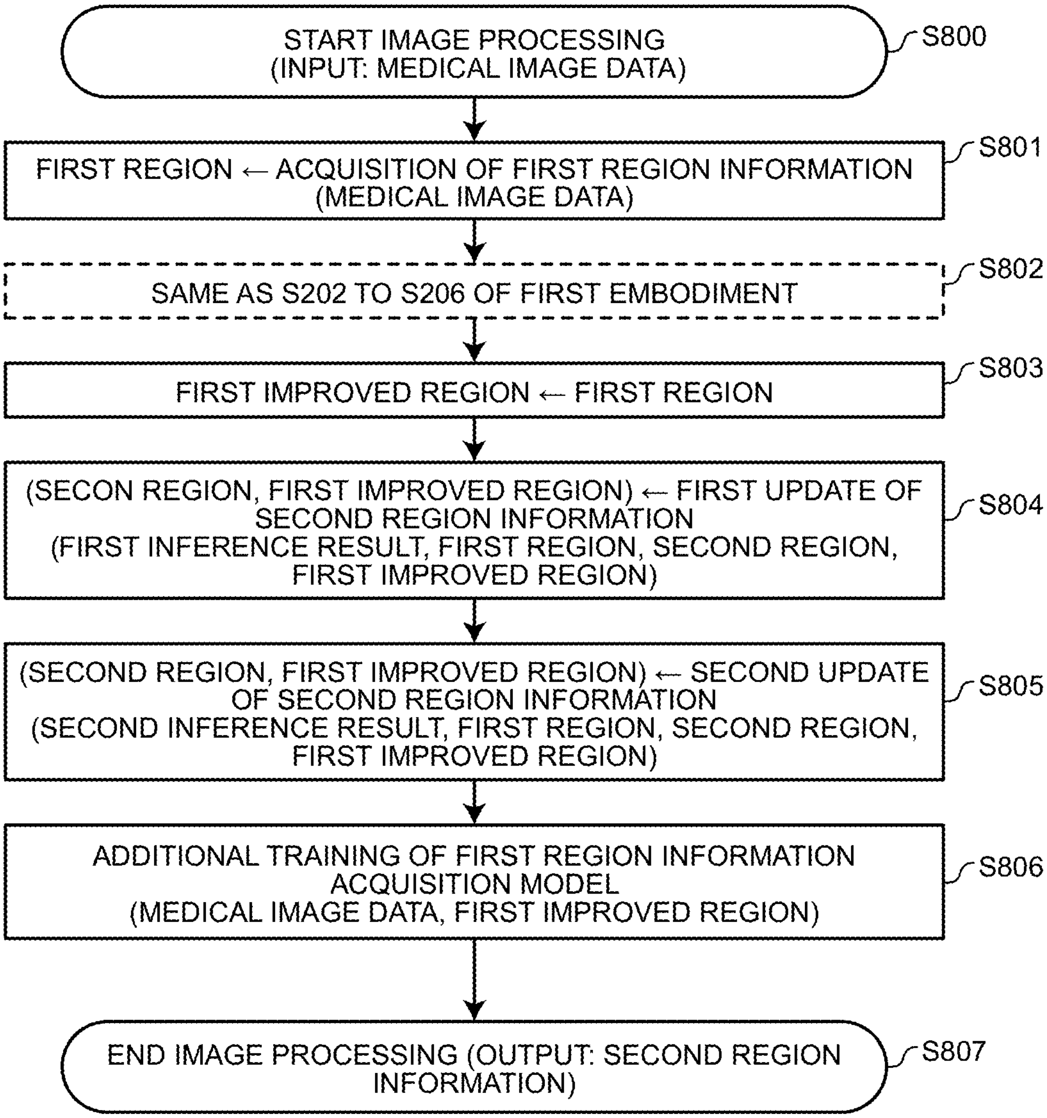
FIG. 8 is a flowchart illustrating an example of a process executed by the image processing apparatus according to the second embodiment.

FIG. 8 is a flowchart illustrating an example of a process implemented by the image processing apparatus 20 according to the second embodiment. Processing illustrated with a dotted frame (Step S802) in FIG. 8 is the same as the processing from Step S202 to Step S206 in FIG. 2. Furthermore, processing from Step S803 to Step S805 illustrated in FIG. 8 is implemented by, for example, the processing circuitry 11 calling and executing a program corresponding to the second region information acquisition function 11*e* from a storage 13. Furthermore, processing at Step S806 illustrated in FIG. 8 is implemented by, for example, the processing circuitry 11 calling and executing a program corresponding to the additional training function 11*f* from the storage 13.

As illustrated by Step S800, the processing circuitry 11 starts image processing, with medical image data serving as input. Furthermore, as illustrated by Step S807, the processing circuitry 11 outputs second region information and a first region information acquisition model described later and ends the image processing. For example, similarly to Step 209, a control function 11*a* performs output of the second region information at Step S807. Furthermore, for example, at Step S807, the control function 11*a* stores the first region information acquisition model into the storage 13 so as to enable the first region information acquisition model to be read and used later.

Step S801

At Step S801, similarly to Step S201 according to the first embodiment, acquisition of first region information is performed. However, in this processing step, a first region is acquired by inference using an inference model based on machine learning. The inference model used herein is a model that has been built for acquisition of the first region but is able to be updated by the additional training function 11*f*. This model is referred to as the first region information acquisition model. The model is updated at a later processing step. That processing step will be described in detail later.

Step S802

At Step S802, processing that is the same as the processing from Step S202 to Step S206 according to the first embodiment is performed.

Step S803

At Step S803, a first improved region is initialized to the first region information. At Steps S804 and S805, this first improved region is updated and is used, at Step S806, for additional training of the first region information acquisition model.

Step S804

Figure 9A:
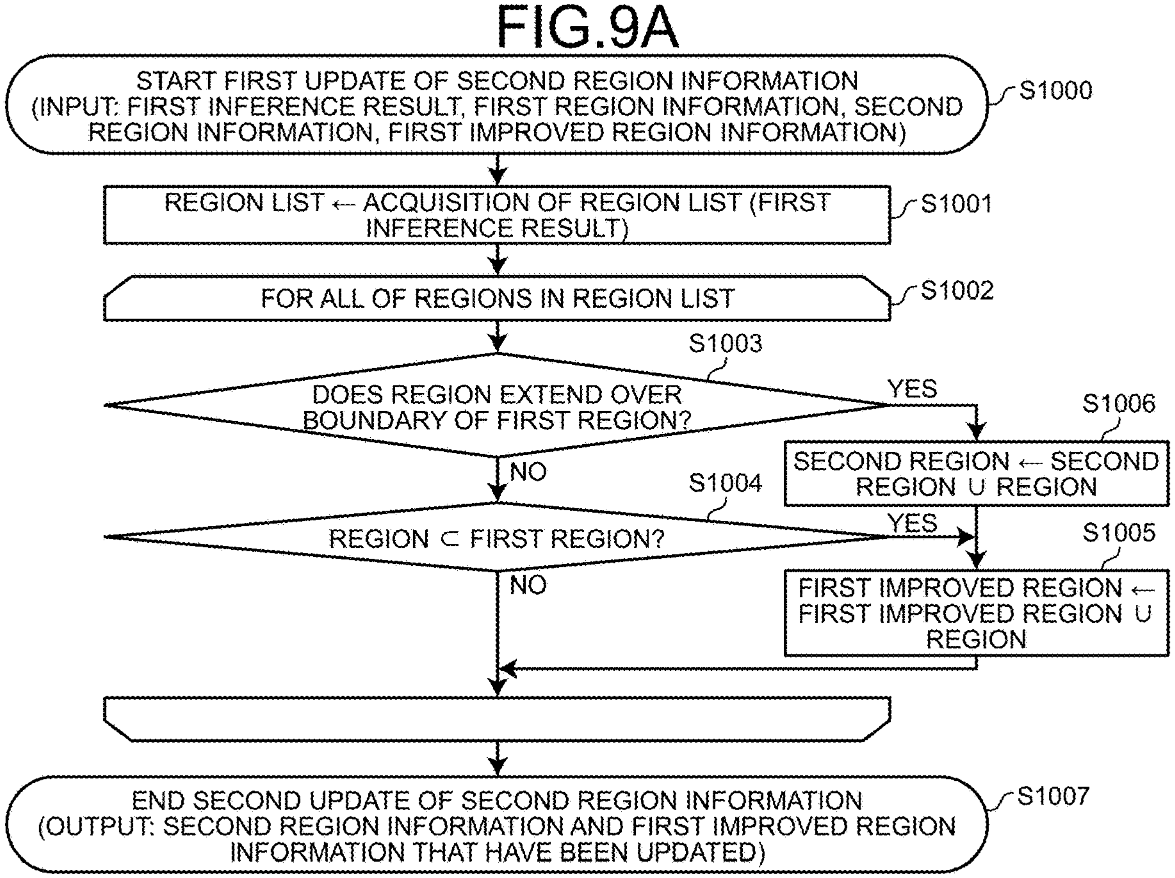
FIG. 9A is a flowchart illustrating an example of update of second region information according to the second embodiment.

At Step S804, the second region information acquisition function 11*e* updates the second region information by using a first inference result and simultaneously updates the first improved region. A specific processing sequence of this processing step will be described in detail by use of FIG. 9A. In the case of FIG. 9A, the second region information acquisition function 11*e* starts a first update of the second region information, with the first inference result, the first region information, the second region information, and first improved region information representing the first improved region all serving as input, as illustrated by Step S1000. Furthermore, the second region information acquisition function 11*e* outputs the second region information and the first improved region information that have been updated and ends the first update of the second region information, as illustrated by Step S1007. Specifically, the second region information and the first improved region information that are output at Step S1007 are stored in, for example, the storage 13 and read and used as appropriate in later processing.

Specifically, at Step S1001, the second region information acquisition function 11*e* acquires a list of regions that are candidates for a second region, from the first inference result, as illustrated by FIG. 9A. Subsequently, Steps S1003 to S1006 are repeated for all of regions in the list of regions. Specifically, at Step S1003, whether or not the region straddles or extends over a boundary of the first region is determined by the conditional expression (1), similarly to Step S603 in FIG. 4A. In a case where a result of the determination is "Yes", the region is a region going out of the first region and the region is thus added to the first improved region at Step S1006. Furthermore, the region is added to the second region at Step S1005. In a case where a result of the determination at Step S1003 is "No", the processing advances to Step S1004, and whether or not the region is completely included in the first region is determined. In a case where a result of this determination is "Yes", the region is added to the second region at Step S1005. In a case where a result of this determination is "No", the region is not added to the second region.

Step S805

Figure 9B:
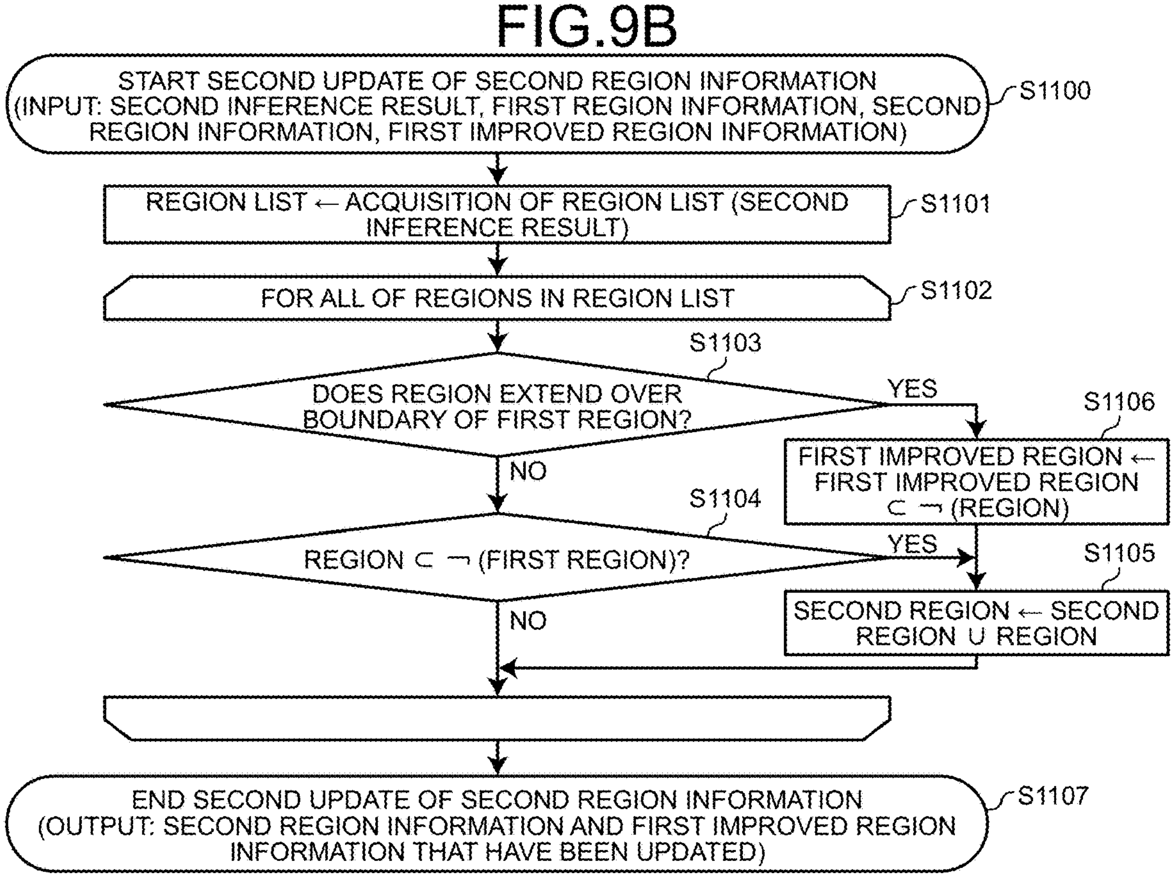
FIG. 9B is a flowchart illustrating an example of update of second region information according to the second embodiment.

Subsequently, as illustrated by Step S805 in FIG. 8, the second region information acquisition function 11*e* updates the second region information by using a second inference result and simultaneously updates the first improved region. A specific processing sequence of this processing step will be described in detail by use of FIG. 9B. In the case of FIG. 9B, the second region information acquisition function 11*e* starts a second update of the second region information, with the second inference result, the first region information, the second region information, and the first improved region information all serving as input, as illustrated by Step S1100. Furthermore, the second region information acquisition function 11*e* outputs the updated second region information and first improved region information and ends the second update of the second region information, as illustrated by Step S1107. Specifically, the second region information and the first improved region information that are output at Step S1107 are stored in, for example, the storage 13 and read and used as appropriate in later processing.

Specifically, at Step S1101, the second region information acquisition function 11*e* acquires a list of regions that are candidates for the second region, from the second inference result, as illustrated by FIG. 9B. Subsequently, Steps S1103 to S1106 are repeated for all of regions in the list of regions. Specifically, at Step S1103, whether or not the region straddles or extends over the boundary of the first region is determined by a conditional expression similar to that at Step S603 in FIG. 4A. In a case where a result of the determination is "Yes", the region is a region that has entered the first region from the outside and the region is thus deleted from the first improved region at Step S1106. Furthermore, the region is added to the second region at Step S1105. In a case where a result of the determination at Step S1103 is "No", the processing advances to Step S1104, and whether or not the region is completely included in a "region outside the first region" is determined. In a case where a result of this determination is "Yes", the region is added to the second region at Step S1105. In a case where a result of this determination is "No", the region is not added to the second region.

The "first improved region" having, added thereto, any region that failed to be extracted as the first region, and deleted therefrom, any region that was extracted superfluously is able to be acquired by the above described processing.

Step S806

Figure 10:
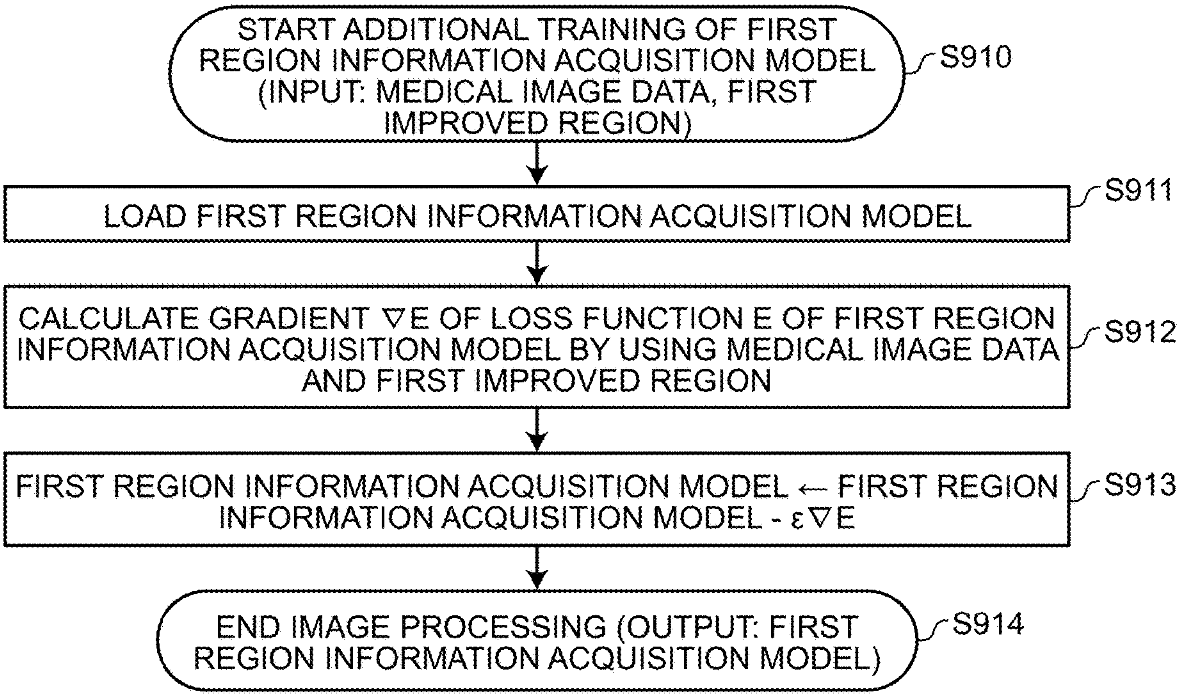
FIG. 10 is a flowchart illustrating an example of additional training of an inference model, according to the second embodiment.

Subsequently, as illustrated by Step S806 in FIG. 8, the additional training function 11*f* performs additional training of the first region information acquisition model by using additional training data that are the medical image data and the first improved region. A specific processing sequence of this processing step will be described in detail by use of FIG. 10. In the case of FIG. 10, the additional training function 11*f* starts the additional training of the first region information acquisition model, with the medical image data and the first improved region information both serving as input, as illustrated by Step S910. Furthermore, as illustrated by Step S914, the additional training function 11*f* outputs the first region information acquisition model that has been additionally trained and ends the additional training. Step S914 in FIG. 10 may be integrated with Step S807 in FIG. 8.

Specifically, the additional training function 11*f* loads the first region information acquisition model from the storage 13 into the processing circuitry 21 at Step S911 as illustrated in FIG. 10. Subsequently, at Step S912, using the medical image data as input and the first improved region as a correct answer, a gradient "$\nabla E$" of a loss function, "E", of the first region information acquisition model is calculated. Subsequently, at Step S913, "ε∇E" is subtracted from the first region information acquisition model and the first region information acquisition model is thereby updated. Herein, "ε" is a learning rate and is set to a sufficiently small value so that the loss function, "E", does not diverge. The method of updating a model according to the second embodiment is just an example, the present invention is not to be limited to this example, and the momentum method or the AdaGrad method may be used instead. Lastly, at Step S914, the first region information acquisition model is saved in the storage 13. The first region information acquisition model to be used at Step S801 is thereby updated. Thereafter, at Step S801, an inference is made using this updated model.

As described above, additional training with the "first improved region" enables acquisition of the "first region" that is higher in precision and increase in precision of the first inference processing.

As described above, using the image processing apparatus according to the embodiment enable improvement in region division precision upon combination of plural models and improvement in the overall inference performance.

The process of acquiring a first inference result or a second inference result using an inference model based on machine learning has been described as the processing at Step S203 or Step S205 according to the first embodiment. The models used in these inferences may be additionally trained using a result of acquisition of the second region. An example of this case will be described as a third embodiment. Medical images will be described as an example of a target to be processed with respect to the third embodiment, but the target to be processed is not limited to medical images.

An overall configuration according to the third embodiment is the same as that of the image processing apparatus 20 according to the second embodiment illustrated in FIG. 7. Processing by an additional training function 11*f* of processing circuitry 21 according to the third embodiment is different from that of the processing circuitry 11 according to the second embodiment. The following description will mainly be on that processing.

Figure 11:
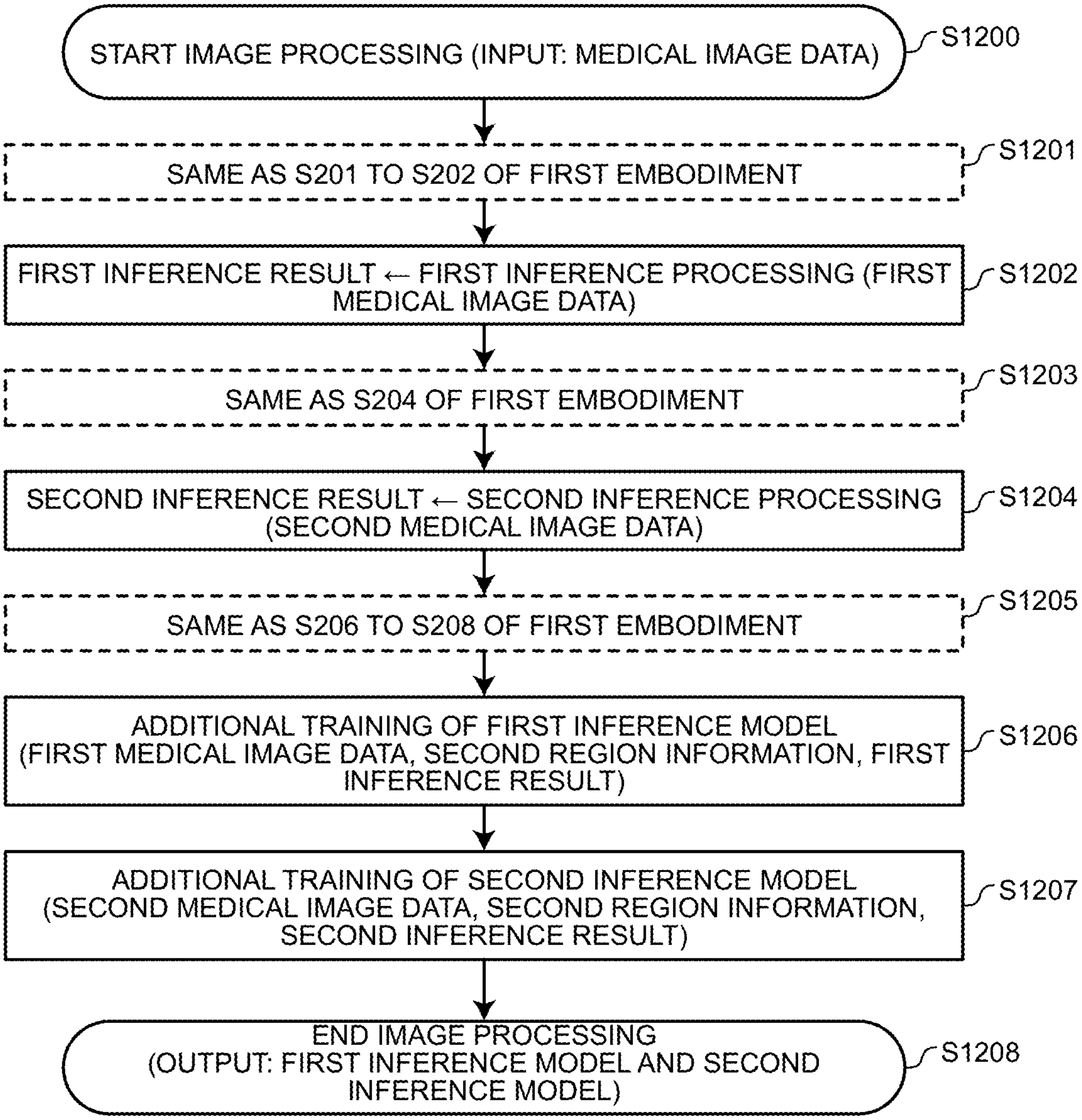
FIG. 11 is a flowchart illustrating an example of a process executed by an image processing apparatus according to a third embodiment.

FIG. 11 is a flowchart illustrating an example of a process implemented by the image processing apparatus 20 according to the third embodiment. Processing illustrated with dotted frames (Steps S1201, S1203, and S1205) in FIG. 11 is the same as that from Step S201 to Step S202, Step S204, and from Step S206 to Step S208, respectively. Furthermore, processing at Steps S1206 and S1207 illustrated in FIG. 11 is implemented by, for example, the processing circuitry 11 calling and executing a program corresponding to the additional training function 11*f*, from a storage 13.

As illustrated by Step S1200, the processing circuitry 11 starts image processing, with medical image data serving as input. Furthermore, as illustrated by Step S1208, the processing circuitry 11 outputs second region information, and a first inference model and a second inference model that have been additionally trained, and ends the image processing. For example, similarly to Step S209, a control function 11*a* performs output of the second region information at Step S1208. Furthermore, for example, at Step S1208, the control function 11*a* stores the first inference model and second inference model, which have been additionally trained, into the storage 13 so as to enable them to be read and used later.

Step S1201

At Step S1201 in FIG. 11, processing that is the same as that from Step S201 to Step S202 according to the first embodiment is performed.

Step S1202

At Step S1202, similarly to Step S203 according to the first embodiment, first inference processing is performed. An inference model used herein is a model that has been built for acquisition of a first inference result but is able to be updated by the additional training function 11*f*. This model will be referred to as the first inference model. The model is updated in a later processing step. That processing step will be described in detail later.

Step S1203

At Step S1203, processing that is the same as that of Step S204 according to the first embodiment is performed.

Step S1204

At Step S1204, similarly to Step S205 according to the first embodiment, second inference processing is performed. An inference model used herein is a model that has been built for acquisition of a second inference result but is able to be updated by the additional training function 11*f*. This model will be referred to as the second inference model. The model is updated in a later processing step. That processing step will be described in detail later.

Step S1205

At Step S1205, processing that is the same as the processing from Step S206 to Step S208 according to the first embodiment is performed.

Step S1206

Subsequently, as illustrated by Step S1206 in FIG. 11, the additional training function 11*f* performs additional training of the first inference model by using first medical image data, a second region, and the first inference result.

A specific processing sequence of Step S1206 will be described in detail by use of FIG. 12. By reference to FIG. 12, the additional training of the first inference model at Step S1206 and additional training of the second inference model at Step S1207 mentioned later will be described collectively. That is, FIG. 12 is a diagram for description of additional training of an N-th inference model, and thus illustrates the processing sequence of Step S1206 in a case where "N=1" and illustrates a processing sequence of Step S1207 in a case where "N=2".

Figure 12:
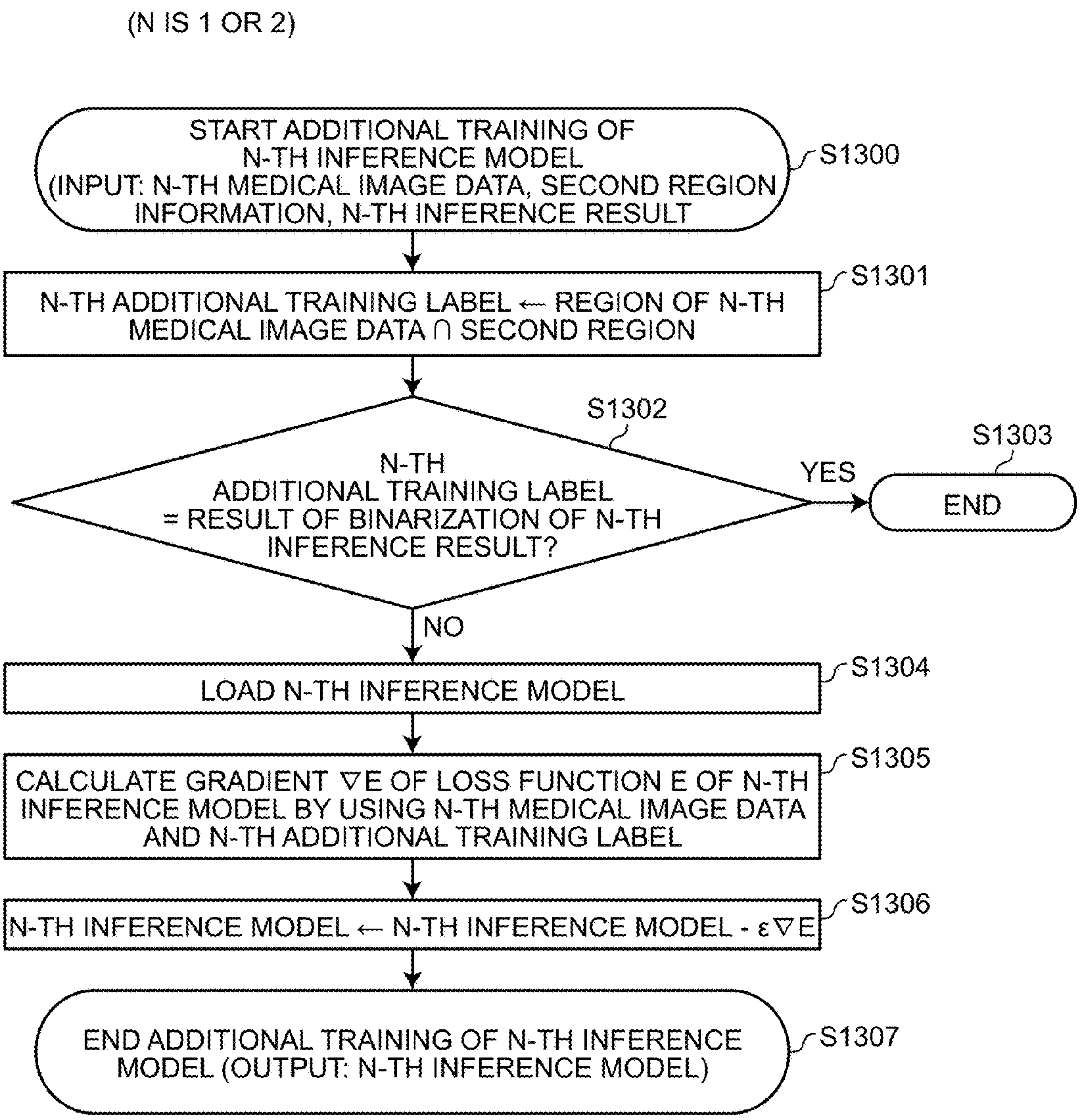
FIG. 12 is a flowchart illustrating an example of additional training of an inference model, according to the third embodiment.

In the case where "N=1" in FIG. 12, the additional training function 11*f* starts the additional training of the first inference model, with the first medical image data, the second region information, and the first inference result all serving as input, as illustrated by Step S1300. Furthermore, as illustrated by Step S1307, the additional training function 11*f* outputs the first inference model that has been additionally trained and ends the additional training. For example, at Step S1307, the additional training function 11*f* stores the first inference model, which has been additionally trained, into the storage 13 so as to enable it to be read and used later.

Specifically, as illustrated in FIG. 12 (in the case where N is 1), the additional training function 11*f* acquires a first additional training label by taking out a portion included in a region of the first medical image data from the second region, at Step S1301. Subsequently, at Step S1302, whether or not the first additional training label and a binarized result of the first inference result are equal to each other is determined. In a case where a result of the determination is "Yes", it is determined that there is no region information worth being used for additional training, the processing advances to Step S1303, and the additional training is ended. In a case where a result of the determination is "No", the processing advances to Step S1304, and the first inference model is loaded into the processing circuitry 21 from the storage 13. Subsequently, at Step S1305, by using the first medical image data as input and the first additional training label as a correct answer, a gradient, "$\nabla E$", of a loss function, "E", of the first inference model is calculated. Subsequently, at Step S1306, "$\varepsilon\nabla E$" is subtracted from the first inference model and the first inference model is thereby updated. Herein, "$\varepsilon$" is a learning rate and is set to a sufficiently small value so that the loss function, "E", does not diverge. The above described method of updating the model is just an example, the third embodiment is not limited to this example, and the momentum method or the AdaGrad method may be used instead.

Step S1207

Subsequently, as illustrated by Step S1207 in FIG. 11, the additional training function 11*f* performs additional training of the second inference model by using second medical image data, the second region, and the second inference result. Specifically, the additional training is done as illustrated in FIG. 12 (the case where N is 2), can be inferred from the case where N is 1, and description thereof will thus be omitted.

The above described processing enables enhancement of extraction of regions by additional training using additional training labels, the regions failing to be extracted in the past by inference using the respective models.

As described above, using the image processing apparatus according to the third embodiment enables improvement in precision of inference for individual lesion candidate regions upon combination of plural models and improvement in the overall inference performance.

Examples of embodiments of the present invention have been described in detail above but the embodiments are not limited to these examples. For example, the present invention may be embodied as a system, an apparatus, a method, a program, or a recording medium (storage medium). Specifically, the present invention may be applied to a system including plural devices (for example, a host computer, an interface device, an imaging device, and a Web application) or may be applied to an apparatus composed of a single device.

The term, "processor" used in the above description means, for example, a circuit, such as a CPU, a graphics processing unit (GPU), an ASIC, or a programmable logic device (for example, a simple programmable logic device (SPLD), a complex programmable logic device (CPLD), or a field programmable gate array (FPGA)). In a case where a processor is a CPU, for example, the processor implements its function by reading and executing a program stored in a storage. In a case where the processor is, for example, an ASIC, instead of the program being stored in the storage, the function is directly incorporated, as a logic circuit, in a circuit of the processor. Each processor according to the embodiments is not necessarily configured as a single circuit, and plural independent circuits may be combined together to be configured as a single processor for their functions to be implemented. Furthermore, plural components in each drawing may be integrated into a single processor for their functions to be implemented.

The components of the apparatuses according to the embodiments described above have been functionally and conceptually illustrated in the drawings and are not necessarily configured physically as illustrated in the drawings. That is, specific modes of separation and integration of each apparatus are not limited to those illustrated in the drawings, and all or part of each apparatus may be configured to be functionally or physically separated or integrated in any units according to various loads and use situations, for example. Furthermore, all or any part of the processing functions executed in the apparatuses may be implemented by a CPU and a program or programs analyzed and executed by the CPU or implemented as hardware by wired logic.

The image processing methods described above with respect to the embodiments may each be implemented by a computer, such as a personal computer or a workstation, executing a program that has been prepared beforehand. This program may be distributed via a network, such as the Internet. Furthermore, this program may be recorded in a computer-readable non-transitory recording medium, such as a hard disk, a flexible disk (FD), a CD-ROM, an MO, or a DVD, and executed by being read by a computer from the recording medium.

At least one of the embodiments described above enables improvement in inference performance in a case where plural models are combined in inference processing based on machine learning for acquisition of region information on lesion candidates.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising processing circuitry configured to acquire medical image data;

acquire, in relation to the medical image data, first region information representing a first region;

acquire a first inference result by a first inference processing of applying a first inference model to first medical image data based on the medical image data, and a second inference result by a second inference processing of applying a second inference model to second medical image data based on the medical image data; and acquire, on the basis of the first region information, second region information that is a region satisfying a predetermined condition, from at least regions based on the first inference result or regions based on the second inference result, wherein the processing circuitry is configured to acquire the second region information that is the region satisfying the predetermined condition, the region being: a region extending from the first region to outside of the first region, the region being among the regions based on the first inference result; or a region extending from the first region to the outside of the first region, the region being among the regions based on the second inference result.

2. The image processing apparatus according to claim 1, wherein the processing circuitry is configured to acquire the second region information that is the region satisfying the predetermined condition, the region being a region extending from the first region to the outside of the first region, the region being among the regions based on the first inference result and the regions based on the second inference result.

3. The image processing apparatus according to claim 1, wherein the processing circuitry is configured not to acquire any region as the second region information by determining that region to be a region not satisfying the predetermined condition, the region being at least one of: a region only present outside the first region, the region being among the regions based on the first inference result; and a region present only in the first region, the region being among the regions based on the second inference result.

4. The image processing apparatus according to claim 1, wherein in a case where the region extending from the first region to the outside of the first region has a predetermined size or more, the processing circuitry is configured to acquire the region as the second region information that is the region satisfying the predetermined condition.

5. The image processing apparatus according to claim 1, wherein in a case where an inference probability for the region extending from the first region to the outside of the first region is equal to or larger than a predetermined value, the processing circuitry is configured to acquire the region as the second region information that is the region satisfying the predetermined condition.

6. The image processing apparatus according to claim 5, wherein in a case where a total sum of inference probabilities for pixels included in the region extending from the first region to the outside of the first region is equal to or larger than a predetermined value, the processing circuitry is configured to acquire the region as the second region information that is the region satisfying the predetermined condition.

7. The image processing apparatus according to claim 1, wherein the processing circuitry is configured to make a determination, on the basis of the first region information, on whether or not at least one of the regions based on the first inference result or the regions based on the second inference result extends from the first region to the outside of the first region, and acquire the second region information on the basis of a result of the determination.

8. The image processing apparatus according to claim 7, wherein the processing circuitry is configured to make the determination on the basis of a contact area between: at least one of the regions based on the first inference result or the regions based on the second inference result; and a boundary of the first region.

9. The image processing apparatus according to claim 1, wherein the processing circuitry is configured to acquire the first region information through inference using a first region information acquisition model, and further perform additional training of the first region information acquisition model by using a region extending from the first region to the outside of the first region, the region being among the regions based on the first inference result and the regions based on the second inference result.

10. The image processing apparatus according to claim 1, wherein the processing circuitry is further configured to perform additional training of the first inference model on the basis of information on a difference between the first inference result and a result of acquisition of the second region information.

11. The image processing apparatus according to claim 1, wherein the processing circuitry is further configured to perform additional training of the second inference model on the basis of information on a difference between the second inference result and a result of acquisition of the second region information.

12. The image processing apparatus according to claim 1, wherein in a case where a region extending from the first region to the outside of the first region is a continuous region, the processing circuitry is configured to acquire the region as the second region information that is the region satisfying the predetermined condition.

13. An image processing method, including:

acquiring medical image data;

acquiring, in relation to the medical image data, first region information representing a first region;

acquiring a first inference result by a first inference processing of applying a first inference model to first medical image data based on the medical image data, and a second inference result by a second inference processing of applying a second inference model to second medical image data based on the medical image data; and acquiring, on the basis of the first region information, second region information that is a region satisfying a predetermined condition, from at least regions based on the first inference result or regions based on the second inference result, wherein a region extending from the first region to outside of the first region, the region being among the regions based on the first inference result, or a region extending from the first region to the outside of the first region, the region being among the regions based on the second inference result, is acquired as the second region information that is the region satisfying the predetermined condition.

14. An image processing apparatus comprising processing circuitry configured to acquire medical image data;

acquire, in relation to the medical image data, first region information representing a first region in a subject;

acquire a first inference result that is a result of first inference processing using a first inference model for first medical image data based on the medical image data, the first inference model having been trained using training data corresponding to a head region of a subject;

acquire a second inference result that is a result of second inference processing using a second inference model for second medical image data based on the medical image data, the second inference model having been trained using training data including at least training data corresponding to a region of the whole body including a head of a subject or training data corresponding to a region of the whole body excluding the head of the subject; and acquire an inference result for the medical image data by integrating the first inference result and the second inference result with each other on the basis of the first region information, wherein in a case where a region is: a region extending from a region corresponding to the first region information to outside of the region corresponding to the first region information, the region being among regions based on the first inference result; or a region extending from the region corresponding to the first region information to the outside of the region corresponding to the first region information, the region being among regions based on the second inference result, the processing circuitry is configured to integrate that region, as a region satisfying a predetermined condition, with the inference result for the medical image data.

15. The image processing apparatus according to claim 14, wherein the processing circuitry is configured not to integrate a region with the inference result by determining the region to be a region not satisfying the predetermined condition, the region being at least one of: a region only present outside the first region, the region being among the regions based on the first inference result; and a region present only in the first region, the region being among the regions based on the second inference result.

* * * * *